(12) United States Patent
Ku et al.

(10) Patent No.: US 10,287,430 B2
(45) Date of Patent: May 14, 2019

(54) METHOD OF MANUFACTURING PATTERNED SUBSTRATE

(71) Applicant: LG Chem, Ltd., Seoul (KR)

(72) Inventors: Se Jin Ku, Daejeon (KR); Mi Sook Lee, Daejeon (KR); Hyung Ju Ryu, Daejeon (KR); Jung Keun Kim, Daejeon (KR); Sung Soo Yoon, Daejeon (KR); No Jin Park, Daejeon (KR); Je Gwon Lee, Daejeon (KR); Eun Young Choi, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/515,432

(22) PCT Filed: Sep. 30, 2015

(86) PCT No.: PCT/KR2015/010338
§ 371 (c)(1),
(2) Date: Mar. 29, 2017

(87) PCT Pub. No.: WO2016/053014
PCT Pub. Date: Apr. 7, 2016

(65) Prior Publication Data
US 2017/0219922 A1      Aug. 3, 2017

(30) Foreign Application Priority Data

Sep. 30, 2014   (KR) .................. 10-2014-0131964
Dec. 8, 2014    (KR) .................. 10-2014-0175400
(Continued)

(51) Int. Cl.
G03F 7/00       (2006.01)
C09D 153/00     (2006.01)
(Continued)

(52) U.S. Cl.
CPC ............ C08L 53/005 (2013.01); B05D 1/005 (2013.01); B05D 3/007 (2013.01);
(Continued)

(58) Field of Classification Search
CPC . G03F 7/0002; G03F 7/30; G03F 7/16; G03F 7/0046; G03F 7/039; G03F 7/162;
(Continued)

(56) References Cited

U.S. PATENT DOCUMENTS 3,976,672 A    8/1976   Strunk et al.
5,115,056 A    5/1992   Mueller et al.
(Continued)

FOREIGN PATENT DOCUMENTS

CN    1333790 A    1/2002
CN    1337974 A    2/2002
(Continued)

OTHER PUBLICATIONS

Palacios et al. (Constructing Robust and Functional Micropatterns on Polystyrene Surfaces by Using Deep UV Irradiation. American Chemical Society, Langmuir (2013), 29(8), pp. 2756-2763).*

(Continued)

*Primary Examiner* — Nadine G Norton
*Assistant Examiner* — Mahmoud Dahimene
(74) *Attorney, Agent, or Firm* — Lerner, David, Littenberg, Krumholz & Mentlik, LLP

(57) ABSTRACT

Provided is a method of manufacturing a patterned substrate. The method may be applied to a process of manufacturing a device such as an electronic device or integrated circuit, or another use, for example, to manufacture an integrated optical system, a guidance and detection pattern of a magnetic domain memory, a flat panel display, a LCD, a thin film magnetic head or an organic light emitting diode, and used to construct a pattern on a surface to be used to manufacture (Continued)

a discrete tract medium such as an integrated circuit, a bit-patterned medium and/or a magnetic storage device such as a hard drive.

24 Claims, 10 Drawing Sheets

(30) Foreign Application Priority Data

| Dec. 8, 2014 | (KR) | 10-2014-0175401 |
|---|---|---|
| Dec. 8, 2014 | (KR) | 10-2014-0175402 |
| Dec. 8, 2014 | (KR) | 10-2014-0175406 |
| Dec. 8, 2014 | (KR) | 10-2014-0175407 |
| Dec. 8, 2014 | (KR) | 10-2014-0175410 |
| Dec. 8, 2014 | (KR) | 10-2014-0175411 |
| Dec. 8, 2014 | (KR) | 10-2014-0175412 |
| Dec. 8, 2014 | (KR) | 10-2014-0175413 |
| Dec. 8, 2014 | (KR) | 10-2014-0175414 |
| Dec. 8, 2014 | (KR) | 10-2014-0175415 |
| Jun. 4, 2015 | (KR) | 10-2015-0079468 |

(51) Int. Cl.

| C08F 293/00 | (2006.01) |
|---|---|
| C08L 53/00 | (2006.01) |
| C08F 212/08 | (2006.01) |
| C08F 216/12 | (2006.01) |
| C08F 220/10 | (2006.01) |
| C08F 220/26 | (2006.01) |
| C08F 220/30 | (2006.01) |
| C08J 5/18 | (2006.01) |
| B05D 1/00 | (2006.01) |
| B05D 3/00 | (2006.01) |
| G03F 7/09 | (2006.01) |
| G03F 7/16 | (2006.01) |
| G03F 7/004 | (2006.01) |
| G03F 7/039 | (2006.01) |
| G03F 7/20 | (2006.01) |
| C08F 32/06 | (2006.01) |
| C08F 299/02 | (2006.01) |
| C08G 61/08 | (2006.01) |
| C08F 2/14 | (2006.01) |
| C08J 7/12 | (2006.01) |
| G03F 7/30 | (2006.01) |
| C08L 53/02 | (2006.01) |
| C08G 61/12 | (2006.01) |
| B81C 1/00 | (2006.01) |
| B82Y 40/00 | (2011.01) |

(52) U.S. Cl.
CPC ............ *B81C 1/00428* (2013.01); *C08F 2/14* (2013.01); *C08F 32/06* (2013.01); *C08F 212/08* (2013.01); *C08F 216/12* (2013.01); *C08F 220/10* (2013.01); *C08F 220/26* (2013.01); *C08F 220/30* (2013.01); *C08F 293/00* (2013.01); *C08F 293/005* (2013.01); *C08F 299/024* (2013.01); *C08G 61/08* (2013.01); *C08G 61/128* (2013.01); *C08J 5/18* (2013.01); *C08J 7/123* (2013.01); *C08L 53/00* (2013.01); *C08L 53/02* (2013.01); *C09D 153/00* (2013.01); *G03F 7/0002* (2013.01); *G03F 7/0046* (2013.01); *G03F 7/039* (2013.01); *G03F 7/091* (2013.01); *G03F 7/16* (2013.01); *G03F 7/162* (2013.01); *G03F 7/2004* (2013.01); *G03F 7/30* (2013.01); *B81C 2201/0149* (2013.01); *B82Y 40/00* (2013.01); *C01P 2002/70* (2013.01); *C07B 2200/00* (2013.01); *C08F 2220/301* (2013.01); *C08F 2438/03* (2013.01); *C08G 2261/1424* (2013.01); *C08G 2261/1426* (2013.01); *C08G 2261/332* (2013.01); *C08G 2261/3324* (2013.01); *C08G 2261/40* (2013.01); *C08G 2261/418* (2013.01); *C08J 2353/00* (2013.01)

(58) Field of Classification Search
CPC ..... G03F 7/2004; G03F 7/091; C09D 153/00; C08F 293/005; C08F 32/06; C08F 2/14; C08F 293/00; C08F 299/024; C08F 212/08; C08F 216/12; C08F 220/10; C08F 220/26; C08F 220/30; C08F 2220/301; C08F 2438/03; C08L 53/005; C08L 53/02; C08L 53/00; B05D 3/007; B05D 1/005; C08G 61/08; C08G 61/128; C08G 2261/1424; C08G 2261/1426; C08G 2261/3324; C08G 2261/418; C08G 2261/40; C08G 2261/332; B81C 1/00428; B81C 2201/0149; C08J 7/123; C08J 5/18; C08J 2353/00; C07B 2200/00; C01P 2002/70; B82Y 40/00
See application file for complete search history.

(56) References Cited

U.S. PATENT DOCUMENTS

| 5,202,402 | A | 4/1993 | Funaki et al. |
|---|---|---|---|
| 5,234,604 | A | 8/1993 | Liao et al. |
| 5,391,626 | A | 2/1995 | Machida et al. |
| 5,418,290 | A | 5/1995 | Machida et al. |
| 5,554,695 | A | 9/1996 | Machida et al. |
| 5,728,431 | A | 3/1998 | Bergbreiter et al. |
| 6,025,437 | A | 2/2000 | Hirahara et al. |
| 6,314,225 | B1 | 11/2001 | Wang |
| 6,531,547 | B1 | 3/2003 | Visger et al. |
| 6,546,282 | B1 | 4/2003 | Inoue et al. |
| 6,953,649 | B2 | 10/2005 | Prat et al. |
| 7,538,159 | B2 | 5/2009 | Wang et al. |
| 8,163,189 | B2 | 4/2012 | Iyoda et al. |
| 8,211,737 | B2* | 7/2012 | Russell ............... B81C 1/00031 438/89 |
| 8,791,042 | B2 | 7/2014 | Ronan et al. |
| 9,495,991 | B2 | 11/2016 | Han et al. |
| 2003/0143343 | A1 | 7/2003 | Kawabata et al. |
| 2004/0049836 | A1 | 3/2004 | Ashraf et al. |
| 2004/0110856 | A1 | 6/2004 | Young et al. |
| 2004/0143032 | A1 | 7/2004 | Auschra et al. |
| 2004/0242787 | A1 | 12/2004 | Chun et al. |
| 2006/0166033 | A1 | 7/2006 | Poetsch et al. |
| 2007/0142559 | A1 | 6/2007 | Wang et al. |
| 2007/0166648 | A1* | 7/2007 | Ponoth .................. G03F 7/0035 430/311 |
| 2007/0219338 | A1 | 9/2007 | Takeda et al. |
| 2008/0105854 | A1 | 5/2008 | Huh et al. |
| 2008/0193658 | A1 | 8/2008 | Millward |
| 2008/0213556 | A1 | 9/2008 | Cha et al. |
| 2008/0286333 | A1 | 11/2008 | Kangas et al. |
| 2008/0311402 | A1 | 12/2008 | Jung et al. |
| 2009/0114108 | A1 | 5/2009 | Oya et al. |
| 2009/0240001 | A1 | 9/2009 | Regner |
| 2009/0253867 | A1 | 10/2009 | Takahashi et al. |
| 2009/0306295 | A1 | 12/2009 | Mays et al. |
| 2010/0086801 | A1 | 4/2010 | Russell et al. |
| 2010/0098876 | A1 | 4/2010 | Hanson |
| 2010/0102415 | A1 | 4/2010 | Millward et al. |
| 2010/0120985 | A1 | 5/2010 | Konishi et al. |
| 2010/0155988 | A1 | 6/2010 | Keil et al. |
| 2010/0206057 | A1 | 8/2010 | Batchelder et al. |
| 2010/0210742 | A1 | 8/2010 | Iyoda et al. |
| 2010/0216312 | A1 | 8/2010 | Yamamoto et al. |
| 2010/0266957 | A1 | 10/2010 | Harada et al. |
| 2010/0285276 | A1 | 11/2010 | Kim et al. |

(56) References Cited

U.S. PATENT DOCUMENTS

| | | |
|---|---|---|
| 2010/0286351 A1 | 11/2010 | Yoshida et al. |
| 2010/0305230 A1 | 12/2010 | Li et al. |
| 2011/0186544 A1 | 8/2011 | Endou et al. |
| 2011/0253946 A1 | 10/2011 | Huh et al. |
| 2011/0294070 A1 | 12/2011 | Hatakeyama et al. |
| 2012/0052446 A1 | 3/2012 | Jaycox et al. |
| 2012/0116024 A1 | 5/2012 | Iyoda et al. |
| 2012/0214094 A1 | 8/2012 | Mikoshiba et al. |
| 2013/0078576 A1 | 3/2013 | Wu et al. |
| 2013/0183828 A1 | 7/2013 | Nakamura et al. |
| 2013/0189504 A1 | 7/2013 | Nealey et al. |
| 2013/0209693 A1 | 8/2013 | Vogel et al. |
| 2013/0209755 A1 | 8/2013 | Hustad et al. |
| 2013/0248488 A1 | 9/2013 | Han et al. |
| 2013/0284698 A1 | 10/2013 | Ogihara |
| 2013/0306594 A1 | 11/2013 | Hustad et al. |
| 2014/0011916 A1 | 1/2014 | Lee et al. |
| 2014/0127456 A1* | 5/2014 | Regner ............... B05D 1/34 428/120 |
| 2014/0141375 A1 | 5/2014 | Cho et al. |
| 2014/0238954 A1 | 8/2014 | Matsumiya et al. |
| 2014/0370442 A1 | 12/2014 | Ober et al. |
| 2015/0064630 A1* | 3/2015 | Wuister ............... C08L 53/00 430/322 |
| 2015/0085042 A1 | 3/2015 | Keoshkerian et al. |
| 2015/0197663 A1 | 7/2015 | Mizutani et al. |
| 2015/0228298 A1 | 8/2015 | Han et al. |
| 2016/0204653 A1 | 7/2016 | Lee |
| 2016/0257838 A1 | 9/2016 | Senzaki et al. |
| 2016/0280823 A1 | 9/2016 | Kim et al. |
| 2016/0280831 A1 | 9/2016 | Park et al. |
| 2016/0280832 A1 | 9/2016 | Kim et al. |
| 2016/0280833 A1 | 9/2016 | Lee et al. |
| 2016/0280834 A1 | 9/2016 | Kim et al. |
| 2016/0280835 A1 | 9/2016 | Lee et al. |
| 2016/0304653 A1 | 10/2016 | Kim et al. |
| 2016/0304654 A1 | 10/2016 | Lee et al. |
| 2016/0304655 A1 | 10/2016 | Lee et al. |
| 2016/0311958 A1 | 10/2016 | Kim et al. |
| 2016/0311959 A1 | 10/2016 | Lee et al. |
| 2016/0311960 A1 | 10/2016 | Lee et al. |
| 2016/0333221 A1 | 11/2016 | Mumtaz et al. |
| 2017/0008992 A1 | 1/2017 | Lee et al. |
| 2017/0058071 A1 | 3/2017 | Lee et al. |
| 2017/0210938 A1 | 7/2017 | Ku et al. |
| 2017/0219922 A1 | 8/2017 | Ku et al. |
| 2017/0226235 A1 | 8/2017 | Park et al. |
| 2017/0226258 A1 | 8/2017 | Lee et al. |
| 2017/0226260 A1 | 8/2017 | Lee et al. |
| 2017/0226261 A1 | 8/2017 | Lee et al. |
| 2017/0247492 A1 | 8/2017 | Choi et al. |
| 2017/0306074 A1 | 10/2017 | Lee et al. |
| 2017/0313869 A1 | 11/2017 | Lee et al. |
| 2018/0170023 A1 | 6/2018 | Park et al. |

FOREIGN PATENT DOCUMENTS

| | | |
|---|---|---|
| CN | 101215362 A | 7/2008 |
| CN | 101443371 A | 5/2009 |
| CN | 101492520 A | 7/2009 |
| CN | 101578232 A | 11/2009 |
| CN | 101688047 A | 3/2010 |
| CN | 101799626 A | 8/2010 |
| CN | 101977839 A | 2/2011 |
| CN | 102172491 A | 9/2011 |
| CN | 102439076 A | 5/2012 |
| CN | 102967918 A | 3/2013 |
| CN | 103025827 A | 4/2013 |
| CN | 103180783 A | 6/2013 |
| CN | 103289285 A | 9/2013 |
| CN | 103562245 A | 2/2014 |
| CN | 103797066 A | 5/2014 |
| CN | 105899556 A | 8/2016 |
| CN | 105899557 A | 8/2016 |
| CN | 105899559 A | 8/2016 |
| CN | 105899560 A | 8/2016 |
| CN | 105934454 A | 9/2016 |
| CN | 105934456 A | 9/2016 |
| CN | 105960422 A | 9/2016 |
| CN | 105980342 A | 9/2016 |
| CN | 106459326 A | 2/2017 |
| CN | 107075052 A | 8/2017 |
| EP | 1141056 B1 | 8/2010 |
| EP | 2781550 A1 | 9/2014 |
| EP | 3078654 A1 | 10/2016 |
| EP | 3078691 B1 | 10/2016 |
| EP | 3078692 A1 | 10/2016 |
| EP | 3078694 A1 | 10/2016 |
| EP | 3203497 A1 | 8/2017 |
| EP | 3214102 A1 | 9/2017 |
| EP | 3225641 A1 | 10/2017 |
| GB | 898065 A | 6/1962 |
| JP | 01260360 A | 10/1989 |
| JP | H01260360 A | 10/1989 |
| JP | H5320281 A | 12/1993 |
| JP | H0665333 A | 3/1994 |
| JP | H10237143 A | 9/1998 |
| JP | H10245427 A | 9/1998 |
| JP | H1143523 A | 2/1999 |
| JP | 2000053734 A | 2/2000 |
| JP | 2000281737 A | 10/2000 |
| JP | 2000285751 A | 10/2000 |
| JP | 3121116 B2 | 12/2000 |
| JP | 2001513125 A | 8/2001 |
| JP | 2001294617 A | 10/2001 |
| JP | 2002145973 A | 5/2002 |
| JP | 2003536105 A | 12/2003 |
| JP | 2004026688 A | 1/2004 |
| JP | 2004323773 A | 11/2004 |
| JP | 2005015508 A | 1/2005 |
| JP | 2005097442 A | 4/2005 |
| JP | 2005148205 A | 6/2005 |
| JP | 2005530030 A | 10/2005 |
| JP | 2005531618 A | 10/2005 |
| JP | 2007070453 A | 3/2007 |
| JP | 2007077292 A | 3/2007 |
| JP | 2007246600 A | 9/2007 |
| JP | 200855579 A | 3/2008 |
| JP | 2009057519 A | 3/2009 |
| JP | 200986354 A | 4/2009 |
| JP | 2009203439 A | 9/2009 |
| JP | 2010507803 A | 3/2010 |
| JP | 2010115832 A | 5/2010 |
| JP | 2010116466 A | 5/2010 |
| JP | 2010145158 A | 7/2010 |
| JP | 2010202723 A | 9/2010 |
| JP | 2010275349 A | 12/2010 |
| JP | 4625901 B2 | 2/2011 |
| JP | 2012001787 A | 1/2012 |
| JP | 2012012577 A | 1/2012 |
| JP | 2012036078 A | 2/2012 |
| JP | 2012093699 A | 5/2012 |
| JP | 2012174984 A | 9/2012 |
| JP | 201368882 A | 4/2013 |
| JP | 2013512323 A | 4/2013 |
| JP | 2013514449 A | 4/2013 |
| JP | 2013121430 A | 6/2013 |
| JP | 2013219334 A | 10/2013 |
| JP | 2013232501 A | 11/2013 |
| JP | 201412807 A | 1/2014 |
| JP | 2014070154 A | 4/2014 |
| JP | 2014102503 A | 6/2014 |
| JP | 2014162504 A | 9/2014 |
| JP | 2015000896 A | 1/2015 |
| JP | 2016539239 A | 12/2016 |
| JP | 2016540863 A | 12/2016 |
| JP | 2017502116 A | 1/2017 |
| JP | 2017505356 A | 2/2017 |
| JP | 2017530236 A | 10/2017 |
| JP | 2017530238 A | 10/2017 |
| JP | 2017533302 A | 11/2017 |
| KR | 20010101356 | 11/2001 |
| KR | 100622353 B1 | 9/2006 |

(56) References Cited

FOREIGN PATENT DOCUMENTS

| | | | |
|---|---|---|---|
| KR | 20090015742 A | 2/2009 | |
| KR | 100935863 B1 | 1/2010 | |
| KR | 20100033962 A | 3/2010 | |
| KR | 20100070380 A | 6/2010 | |
| KR | 20100123920 A | 11/2010 | |
| KR | 20110018678 A | 2/2011 | |
| KR | 20110086834 A | 8/2011 | |
| KR | 20110097707 A | 8/2011 | |
| KR | 20110102998 A | 9/2011 | |
| KR | 20110112501 A | 10/2011 | |
| KR | 101102680 B1 | 1/2012 | |
| KR | 20120119998 A | 11/2012 | |
| KR | 20130094264 A | 8/2013 | |
| KR | 20130113596 A | 10/2013 | |
| KR | 20130128346 A | 11/2013 | |
| KR | 20140063790 A | 5/2014 | |
| KR | 20150066488 A | 6/2015 | |
| KR | 20150067065 A | 6/2015 | |
| KR | 20150067069 A | 6/2015 | |
| KR | 20150067070 A | 6/2015 | |
| KR | 20160038705 A | 4/2016 | |
| TW | 201323461 A | 6/2013 | |
| TW | 201428046 A | 7/2014 | |
| TW | 201536823 A | 10/2015 | |
| TW | 201538548 A | 10/2015 | |
| WO | 9837136 A1 | 8/1998 | |
| WO | 2007055371 A1 | 5/2007 | |
| WO | 2012144735 A2 | 10/2012 | |
| WO | 2013069544 A1 | 5/2013 | |
| WO | 2013120051 A1 | 8/2013 | |
| WO | 2013158527 A1 | 10/2013 | |
| WO | 2014050905 A1 | 4/2014 | |
| WO | 2014090178 A1 | 6/2014 | |
| WO | 2014124795 A1 | 8/2014 | |
| WO | 2015084121 A1 | 6/2015 | |
| WO | 2015084122 A1 | 6/2015 | |
| WO | 2015084123 A1 | 6/2015 | |
| WO | 2015084124 A1 | 6/2015 | |
| WO | 2015084125 A1 | 6/2015 | |
| WO | 2015084126 A1 | 6/2015 | |
| WO | 2015084127 A1 | 6/2015 | |
| WO | 2015087005 A1 | 6/2015 | |
| WO | 2016052994 A1 | 4/2016 | |
| WO | 2016052999 A1 | 4/2016 | |
| WO | 2016053005 A1 | 4/2016 | |
| WO | 2016053007 A1 | 4/2016 | |
| WO | 2016053011 A1 | 4/2016 | |

OTHER PUBLICATIONS

CN Search Report for Application No. 201480071920.0 dated Aug. 2, 2017.
CN Search Report for Application No. CN201480072884.X dated Aug. 3, 2017.
CN Search Report for Application No. CN2014800740447 dated Aug. 1, 2017.
Extended European Search Report for Application No. EP14867273 dated Aug. 10, 2017.
Mariana Beija et al: "Fluorescence Anisotropy of Hydrophobic Probes in poly(N-decylacrylamide) block-poly( N, N-diethylacrylamide) Block Copolymer Aqueous Solutions: Evidence of Premicellar Aggregates" Journal of Physical Chemistry Part B: Condensed Matter, Materials, Surfaces, Interfaces & Bi0physical, vol. 114, No. 31, Aug. 12, 2010 (Aug. 12, 2010), 9977-9986, XP055394763, US ISSN: 1520-6106, D0I: 10.1021/jp101613y abstract Scheme 1, PDcA11-block-PDEA295; p. 9978.
Riedel et al., Synthesis, post-modification and self-assembled thin films of pentafluorostyrene containing block copolymers, European Polymer Journal 47 (2011) 675-684.
Yoshida, E. et al. Polymer Journal vol. 31 (5) pp. 429-434 (1999).
U.S. Appl. No. 15/102,139, filed Jun. 6, 2016.
U.S. Appl. No. 15/102,149, filed Jun. 6, 2016.
U.S. Appl. No. 15/102,156, filed Jun. 6, 2016.
U.S. Appl. No. 15/173,670, filed Jun. 5, 2016.
U.S. Appl. No. 15/173,671, filed Jun. 5, 2016.
U.S. Appl. No. 15/173,673, filed Jun. 5, 2016.
U.S. Appl. No. 15/173,674, filed Jun. 5, 2016.
U.S. Appl. No. 15/173,676, filed Jun. 5, 2016.
U.S. Appl. No. 15/514,929, filed Mar. 28, 2017.
U.S. Appl. No. 15/514,939, filed Mar. 28, 2017.
U.S. Appl. No. 15/514,959, filed Mar. 28, 2017.
U.S. Appl. No. 15/514,967, filed Mar. 28, 2017.
U.S. Appl. No. 15/515,290, filed Mar. 29, 2017.
U.S. Appl. No. 15/515,293, filed Mar. 29, 2017.
U.S. Appl. No. 15/515,812, filed Mar. 30, 2017.
U.S. Appl. No. 15/515,818, filed Mar. 30, 2017.
U.S. Appl. No. 15/515,821, filed Mar. 30, 2017.
Akiba, Isamu, et al., "Self-Assembly of Amphiphilic Block Copolymers Containing Poly(n-octadecyl acrylate) Block in Aqueous Solution." IOP Conference Series: Materials Science and Engineering, 2010, vol. 14, No. 1, pp. 1-8.
Hua et al. Temperature-induced phase-transitions of methoxyoligo(oxyethylene) styrene-based block copolymers in aqueous solution, Soft Matter, 2013, 9, 8897.
International Search Report from PCT/KR2014/012023, dated Mar. 10, 2015.
International Search Report from PCT/KR2014/012024, dated Mar. 17, 2015.
International Search Report from PCT/KR2014/012025, dated Mar. 17, 2015.
International Search Report from PCT/KR2014/012026, dated Mar. 17, 2015.
International Search Report from PCT/KR2014/012027, dated Mar. 17, 2015.
International Search Report from PCT/KR2014/012028, dated Mar. 17, 2015.
International Search Report from PCT/KR2014/012029, dated Mar. 17, 2015.
International Search Report from PCT/KR2014/012030, dated Mar. 17, 2015.
International Search Report from PCT/KR2014/012031, dated Feb. 12, 2015.
International Search Report from PCT/KR2014/012032, dated Feb. 12, 2015.
International Search Report from PCT/KR2014/012033, dated Feb. 12, 2015.
International Search Report from PCT/KR2014/012034, dated Feb. 12, 2015.
International Search Report from PCT/KR2014/012035, dated Feb. 12, 2015.
International Search Report from PCT/KR2014/012036, dated Mar. 17, 2015.
International Search Report from PCT/KR2015/010313, dated Nov. 23, 2015.
International Search Report from PCT/KR2015/010320, dated Jan. 13, 2016.
International Search Report from PCT/KR2015/010322, dated Jan. 13, 2016.
International Search Report from PCT/KR2015/010323, dated Jan. 13, 2016.
International Search Report from PCT/KR2015/010327, dated Jan. 12, 2016.
International Search Report from PCT/KR2015/010330 dated Jan. 11, 2016.
International Search Report from PCT/KR2015/010332 dated Jan. 13, 2016.
International Search Report from PCT/KR2015/010334, dated Jan. 13, 2016.
International Search Report from PCT/KR2015/010335 dated Jan. 13, 2016.
International Search Report from PCT/KR2015/010338 dated Jan. 14, 2016.
IPO Search Report from Taiwan Application No. 103142745, dated Dec. 14, 2015.

(56) References Cited

OTHER PUBLICATIONS

IPO Search Report from Taiwan Application No. 103142777, dated Dec. 15, 2015.
IPO Search Report from Taiwan Application No. 103142780, dated Dec. 15, 2015.
IPO Search Report from Taiwan Application No. 103142784, dated Jan. 27, 2016.
IPO Search Report from Taiwan Application No. 103142786, dated Jan. 11, 2016.
IPO Search Report from Taiwan Application No. 103142790, dated Dec. 15, 2015.
IPO Search Report from Taiwan Application No. 103142794, dated Dec. 15, 2015.
IPO Search Report from Taiwan Application No. 103142798, dated Dec. 16, 2015.
IPO Search Report from Taiwan Application No. 103142805, dated Dec. 11, 2015.
IPO Search Report from Taiwan Application No. 103142955, dated Jan. 15, 2016.
IPO Search Report from Taiwan Application No. 103142956 dated Jan. 20, 2016.
IPO Search Report from Taiwan Application No. 103142963, dated Dec. 10, 2015.
IPO Search Report from Taiwan Application No. 104132186, dated Aug. 18, 2016.
IPO Search Report from Tawain Application No. 103142782, dated Dec. 11, 2015.
Khazimullis et al. "Gel formation in a mixture of a block copolymer and a nematic liquid crystal", Physical Review E 84, 021710 (2011).
Park et al., "Block Copolymer Lithography: Periodic Arrays of ~10 11 Holes in 1 Square Centimeter", Science 276, p. 1401-1404, May 30, 1997.
Tenneti et al. "Competition between liquid crystallinity and block copolymer self-assembly in core-shell rod-coil block copolymers", Soft Matter, 2008, 4, 458-461 (2008).
Tenneti et al. Hierarchical Nanostructures of Mesogen Jacketed Bent-Core Liquid Crystalline Block Copolymers, Proceedings Published 2007 by the American Chemical Society.
U.S. Appl. No. 15/101,794, filed Jun. 3, 2016.
U.S. Appl. No. 15/101,812, filed Jun. 3, 2016.
U.S. Appl. No. 15/101,827, filed Jun. 3, 2016.
U.S. Appl. No. 15/101,915, filed Jun. 5, 2016.
U.S. Appl. No. 15/102,089, filed Jun. 6, 2016.
U.S. Appl. No. 15/102,112, filed Jun. 6, 2016.
Database CA [Online] Chemical Abstracts Service Ohi0 US; Zou, Yue: "Fluorosurfactant capable of preventing unevenness in photoresist coating and its preparation by anionic polymerization", XP002771143 retrieved from STN Database accession No. 2011:1148166 abstract & CN 102 172 491 A (Jiangsu Johnny Material Technology Co Ltd) Sep. 7, 2011 (Sep. 7, 2011) Columbus, No. 2011:1148166.
European Search Report for Application No. EP14867501 dated Jul. 14, 2017.
Kago K et al: "X-ray reflectivity of polymer assembly at air-water interface" Supramolecular Science Butterworth-Heinemann Oxford GB vol. 5 No. 3-4, Jul. 1, 1998 (Jul. 1, 1998)pp. 349-355 XP027388373 ISSN: 0968-5677 [retrieved on Jul. 1, 1998]abstract.
Lutz Funk et al: "Novel Amphiphilic Styrene-Based Block Copolymers for Induced Surface Reconstruction". Macromolecular Chemistry and Physics., vol. 209, No. 1, Jan. 4, 2008 (Jan. 4, 2008), XP055382259 DE ISSN: 1022-1352 D0I: 10.1002/macp.200700312 scheme 1, monomers M1, M4 table 2.
Mori H et al: "Synthesis and Surface Characterizati0n of Hydrophilic-Hydrophobic Block Copolymers Containing Poly(2, 3-Dihydroxypropyl Methacrylate) "Macromolecules American Chemical Society US vol. 27 No. 15 Jul. 18, 1994 (Jul. 18, 1994) pp. 4093-4100 XP000456650 ISSN: 0024-9297 D0I: 10.1021/MA00093A010 abstract.

Anonymous., "Solid surface energy data (SFE) for common polymers", surface-tension.de, Feb. 2017, Retreived from the Internet: URL:http://www.surface-tension.de/solid-surface-energy.htm, XP002775246.
Cummins et al., "Solvothermal Vapor Annealing of Lamellar Poly(styrene)-block-poly(D,L-lactide) Block Copolymer Thin Films for Directed Self-Assembly Application", ACS Applied Materials & Interfaces, Mar. 2016, vol. 8, No. 12, pp. 8295-8304, XP055419698.
Extended European Search Report for Application No. EP14867808.9 dated Nov. 10, 2017.
Extended European Search Report for Application No. EP14868022.6 dated Nov. 6, 2017.
Extended European Search Report for Application No. EP14868320.4 dated Nov. 20, 2017.
Extended European Search Report for Application No. EP14868480.6 dated Nov. 2, 2017.
Hvilsted et al., "Novel Fluorinated Polymer Materials Based on 2,3,5,6-Tetrafluoro-4-methoxyystyrene" In: "Advances in Controlled/Living Radical Polymerization", American Chemical Society, Jun. 26, 2003, vol. 854, pp. 236-249, XP055421064.
Mahajan et al., "Synthesis and Characterization of Amphiphilic Poly(ethylene oxide)-block-poly(hexylmethacrylate Copolymers", Macromolecular Chemistry and Physics, Wiley-Vch Verlag, Weinheim, DE, Jan. 2003, vol. 204, pp. 1047-1055, XP003030406.
Pochan et al., "Morphologies of microphase-seperated conformationally asymmetric diblock copolymers", Journal of Polymer Science Part B: Polymer Physics, Nov. 2017, vol. 35, No. 16, pp. 2629-2643, XP055417266.
Zhuang et al., "Synthesis of A-B type block copolymers using 1-phenylethyl dithiobenzoate as Reversible Addition-Fragmentation Chain Transfer agent", Database CA [online], Chemical Abstracts Service, Columbus, OH, XP002775247.
Beng H. Tan et al, "Synthesis and Self-Assembly of pH-Responsive Amphiphilic Poly (dimethylaminoethylmethacrylate)-block-Poly(pentafluorostyrene) Block Copolymer in Aqueous Solution", Macromolecular Rapid Communications, 2009, vol. 30, pp. 1002-1008.
Chinese Search Report for CN Application No. 201480074044.7 dated Jun. 7, 2018.
Frank S. Bates et al., "Block Copolymer Thermodyanmics: Theory and Experiment", Annu. Rev. Phys. Chem., 1990, vol. 41, pp. 525-557.
G.R. Strobl, "The Physics of Polymers: Concepts for Understanding Their Structures and Behavior", Springer (Abstract Only).
S. Chavda et al., "Synthesis of stimuli responsive PEG47-b-PAA126-b-PSt32 triblock copolymer and its self-assembly in aqueous solutions", European Polymer Journal, Sep. 2012, vol. 49, pp. 209-216.
Sachin Borkar et al., "New Highly Fluorinated Styrene-Based Materials with Low Surface Energy Prepared by ATRP", Macromolecules, Jan. 2004, vol. 37, pp. 788-794.
Chinese Search Report for Application No. 201480072759.9 dated Jan. 24, 2018.
Chinese Search Report for Application No. 2014800727599 dated Jan. 8, 2018.
Chinese Search Report for Application No. 2014800741401 dated Mar. 9, 2018.
Chinese Search Report for Application No. 201480074156.2 dated Apr. 3, 2018.
Chinese Search Report for CN Application No. 201480071920.0, dated May 4, 2018.
Chinese Search Report for CN Application No. 201480072800.2, dated Apr. 10, 2018.
Chinese Search Report for CN Application No. 201480074045.1, dated Apr. 11, 2018.
Extended European Seach Report including Written Opinion for EP Application No. 15847574.9, dated May 3, 2018.
Extended European Search Report including Written Opinion for EP Application No. 15845928.9, dated May 2, 2018.
Extended European Search Report including Written Opinion for EP Application No. 15847598.8, dated May 11, 2018.
Extended European Search Report including Written Opinion for EP15845720.0 dated May 4, 2018.

(56) References Cited

OTHER PUBLICATIONS

Extended European Search Report with Written Opinion for EP15846832.2 dated May 3, 2018.
Funk, L. et al., "Novel Amphiphilic Styrene-Based Block Copolymers for Induced Surface Reconstruction," Macromolecular Chemistry and Physics, vol. 209, No. 1, Jan. 4, 2008, pp. 52-63, XP055382259, DE, ISSN: 1022-1352, DOI: 10.1002/macp.200700312.
Haeng-Dong Koh et al., "Location-controlled parallel and vertical orientation by dewetting-induced block copolymer directed self-assembly," Journal of Materials Chemistry C: Materials for Optical and Electronic Devices, vol. 1, No. 25, Jan. 1, 2013, pp. 4020-4024 XP055469744.
Ma J et al., "Synthesis and Solution-State Assembly or Buld State Thiol-ene Crosslinking of Pyrrolidinone- and Alkene-Functionalized Amphiphilic Block Fluorocopoplymers: From Functional Nanoparticles to Anti-Fouling Coatings", Australian Journal of Chemistry: An International Journal for Chemical Sci, Jan. 1, 2010, pp. 1159-1163, vol. 63, No. 8,CSIRO Publishing, Australia.
Mori H. et al., "Synthesis and Surface Characterization of Hydrophilic-Hydrophobic Block Copolymers Containing Poly(2,3-dihydroxypropyl methacrylate)," Macromolecules, American Chemical Society, US, vol. 27, No. 15, Jul. 18, 1994, pp. 4093-9297; XP000456650, DOI: 10.2021/MA00093A010.
Segalman R.A. et al., "Graphoepitaxy of Spherical Domain Block Copolymer Films," Advanced Materials, Wiley-VCH Verlag GmbH & Co. KGAA, DE, vol. 13, No. 15, Aug. 3, 2001, pp. 1152-1155; XP001129643, ISSN: 0935-9648, DOI: 10.1002/1521-4095(200108)13:15<1152: AID-A DMA1152>3.0.CO; 2-5.
Supplementary European Search Report for EP15847157 dated Mar. 21, 2018.
C.M. Bates et al., "Polymeric Cross-Linked Surface Treatments for Controlling Block Copolymer Orientation in Thin Films", Langmuir Article, American Chemical Society, Jan. 7, 2011, vol. 27, No. 5, pp. 1-7.
Chakrabarty, et al., "Tailor-Made Polyfluoroacrylate and its Block Copolymer by RAFT Polymerization in Miniemulsion; Improved Hydrophobicity in the Core-Shell Block Copolymer", Journal of Colloid and Interface Science, vol. 408, Oct. 2013, pp. 66-74.
EESR for EP Application No. 15847536.8 dated Aug. 23, 2018, 6 pages.
Extended European Search Report including Written Opinion for Application No. EP15845665.7 dated Jun. 27, 2018.
Gregory, et al., "Complex Polymer Architectures via RAFT Polymerization: From Fundamental Process to Extending the Scope Using Click Chemistry and Nature's Building Blocks", Progress in Polymer Science, vol. 37, No. 1, Jan. 2012, pp. 38-105.
Katja Nilles et al., "RAFT Polymerization of Activated 4-Vinylbenzoates"., Journal of Polymer Science: Part A: Polymer Chemistry, Jan. 1, 2009, vol. 47, pp. 1696-1705.
Truelsen et al., "Synthesis by ATRP of triblock copolymers with densely grafted styrenic end blocks from a polyisobutylene macroinitiator", Marcomol. Rapid. Commun., Jul. 2, 1999, vol. 21, No. 2, pp. 1-5.
Chinese Search Report for Application No. CN201580059758.5 dated Sep. 5, 2018.
Chinese Search Report for Application No. CN201580060097.8 dated Sep. 19, 2018.
CN Search Report for Application No. CN201580059710.4. dated Sep. 3, 2018.
Extended European Search Report including Written Opinion for EP Application 15846126.9 dated Sep. 12, 2018.
Kobayashi S, Matsuzawa T, Matsuoka SI, Tajima H, Ishizone T. Living Anionic Polymerizations of 4-(1-Adamantyl)styrene and 3-(4-Vinylphenyl)-1, 1'-biadamantane. Macromolecules. Sep. 5, 2006;39(18):5979-86.

\* cited by examiner

A B

METHOD OF MANUFACTURING PATTERNED SUBSTRATE

CROSS-REFERENCE TO RELATED APPLICATIONS

The present application is a national phase entry under 35 U.S.C. § 371 of International Application No. PCT/KR2015/010338, filed Sep. 30, 2015, published in Korean, which claims priority to and the benefit of Korean Patent Application No. 2014-0131964, filed on Sep. 30, 2014, No. 2015-0079468, filed on Jun. 4, 2015, No. 2014-0175411, filed on Dec. 8, 2014, No. 2014-0175414, filed on Dec. 8, 2014, No. 2014-0175410, filed on Dec. 8, 2014, No. 2014-0175415, filed on Dec. 8, 2014, No. 2014-0175412, filed on Dec. 8, 2014, No. 2014-0175413, filed on Dec. 8, 2014, No. 2014-0175407, filed on Dec. 8, 2014, No. 2014-0175406, filed on Dec. 8, 2014, No. 2014-0175400, filed on Dec. 8, 2014, No. 2014-0175401, filed on Dec. 8, 2014, and No. 2014-0175402, filed on Dec. 8, 2014, the disclosures of which are incorporated herein by reference in their entirety.

FIELD

The present application relates to a method of manufacturing a patterned substrate.

BACKGROUND

A block copolymer has a molecular structure in which polymer blocks having different chemical structures are linked by covalent bonds. The block copolymer may form a periodically arranged structure such as a sphere, a cylinder or a lamella through phase separation. The shape and size of a domain of the structure formed by self assembly of the block copolymer may be controlled in a wide range by, for example, the type of a monomer forming each block or the relative ratio of blocks.

Due to such a characteristic, the block copolymer is considered to be applied to lithographic process that can manufacture nanowires, manufacture various next generation nano elements such as quantum dots or metal dots, or form a high density pattern on a predetermined substrate (e.g., refer to Non-patent document 1).

The technology of controlling orientation of the structure in which the block copolymers are self-assembled on various types of substrates horizontally or vertically is a very big part of practical application of the block copolymer. Conventionally, the orientation of a nano structure on a film of the block copolymer is determined by which block is exposed to a surface or in the air. Generally, since a plurality of substrates are polar and the air is non-polar, among blocks of the block copolymer, a block having a higher polarity is wetted on a substrate, and a block having a lower polarity is wetted at an interface between the block and the air. Accordingly, to simultaneously wet blocks of the block copolymer, which have different characteristics, on a substrate, various techniques are suggested, and the most typical technique is control of orientation through manufacture of a neutral surface.

Non-Patent Document (Non-patent document 1) Chaikin and Register. et al., Science 276, 1401 (1997)

DESCRIPTION

Object

The present application is directed to providing a method of manufacturing a patterned substrate.

Solution

The term "alkyl group" used herein may refer to, unless particularly defined otherwise, an alkyl group having 1 to 20, 1 to 16, 1 to 12, 1 to 8, or 1 to 4 carbon atoms. The alkyl group may be a linear, branched or cyclic alkyl group, and may be optionally substituted with one or more one substituent.

The term "alkoxy group" used herein may refer to, unless particularly defined otherwise, an alkoxy group having 1 to 20, 1 to 16, 1 to 12, 1 to 8, or 1 to 4 carbon atoms. The alkoxy group may be a linear, branched or cyclic alkoxy group, and may be optionally substituted with one or more substituent.

The term "alkenyl group" or "alkynyl group" used herein may refer to, unless particularly defined otherwise, an alkenyl group or alkynyl group having 2 to 20, 2 to 16, 2 to 12, 2 to 8, or 2 to 4 carbon atoms. The alkenyl group or alkynyl group may be a linear, branched or cyclic alkenyl or alkynyl group, and may be optionally substituted with one or more substituent.

The term "alkylene group" used herein may be, unless particularly defined otherwise, an alkylene group having 1 to 20, 1 to 16, 1 to 12, 1 to 8, or 1 to 4 carbon atoms. The alkylene group may be a linear, branched or cyclic alkylene group, and may be optionally substituted with one or more substituent.

The term "alkenylene group or alkynylene group" used herein may refer to, unless particularly defined otherwise, an alkenylene or alkynylene group having 2 to 20, 2 to 16, 2 to 12, 2 to 8, or 2 to 4 carbon atoms. The alkenylene group or alkynylene group may be a linear, branched or cyclic alkenylene or alkynylene group, and may be optionally substituted with one or more substituent.

The term "single bond" used herein may refer to the case in which a separate atom is not present in the corresponding part. For example, when B is a single bond in the structure represented as A-B-C, a separate atom is not present in the part represented by B, and A and C are directly linked, thereby forming the structure represented by A-C.

In the present application, as a substituent that can be optionally substituted in an alkyl group, an alkenyl group, an alkynyl group, an alkylene group, an alkenylene group, an alkynylene group, an alkoxy group, an aryl group, an arylene group, or a chain or aromatic structure, a hydroxyl group, a halogen atom, a carboxyl group, a glycidyl group, an acryloyl group, a metacryloyl group, an acryloyloxy group, a metacryloyloxy group, a thiol group, an alkyl group, an alkenyl group, an alkynyl group, an alkylene group, an alkenylene group, an alkynylene group, an alkoxy group or an aryl group may be used, but the present application is not limited thereto.

The present application relates to a method of manufacturing a patterned substrate. In one embodiment, the manufacturing method may be performed by lithographic process using a directed self-assembly material as a template. Here, the directed self-assembly material may be, for example, a block copolymer.

The method may be applied to, for example, a process of manufacturing devices such as an electronic device and an integrated circuit or a different use such as manufacture of an integrated optical system, a guidance and a test pattern of a magnetic domain memory, a flat display, a liquid crystal display (LCD), a thin film magnetic head or an organic light emitting diode. The method may also be used to construct a pattern on a surface used to manufacture an integrated circuit, a bit-patterned medium and/or a discrete track medium such as a hard drive.

The method may include forming a layer of a directed self-assembly material on a substrate on which a template is formed, and inducing the self-assembly. In the above, the template may include mesa structures that are arranged on the substrate and are spaced from each other. A trench may be formed on the substrate by the mesa structures and the self-assembly material such as a block copolymer may be formed within the trench.

A type of the substrate applied to the method of the present application is not particularly limited. As an illustrative substrate to which the method of the present application is applied, various substrate such as a substrate required to have a pattern on its surface in order to be used in the above-described application may be used. This kind of substrate, for example, may be a semiconductor substrate such as a silicon substrate, a silicon germanium substrate, GaAs substrate, silicon oxide substrate. The substrate, for example, in a substrate that is applied to the formation of other electronic devices such as fin field effect transistor (finFETs) or a diode, transistors or capacitors may be used. In addition, other materials also may be used as the substrate of ceramic or the like according to the application, type of substrate that can be applied in the present application is not particularly limited.

On the surface of the substrate used in the present method, mesa structures may be formed and arranged with an interval between them. For example, each of the mesa structures may have a line shape. Such mesa structures may be disposed apart from each other at regular intervals on the surface of the substrate. The mesa structures may be disposed substantially parallel to each other on the surface of the substrate. Two or more mesa structures may be formed on the surface of the substrate. That is, the number of trenches formed by the mesa structures on the surface of the substrate may be one or more. The numbers of the mesa structures and trenches may be controlled depending on their uses without particular limitation. The mesa structures may serve to guide the self-assembly structure of the block copolymer formed when a film including the directed self-assembly material such as the block copolymer is formed in the trench formed by the mesa structures.

FIG. 1 shows an illustrative substrate 1 in which a trench is formed. The illustrative substrate 1 shown in FIG. 1 may include a side wall 3 having a mesa structure, and a trench 2 formed by the substrate or a surface 4 having the mesa structure.

For example, as shown in FIG. 2, a film 5 including a directed self-assembly material such as a block copolymer may be formed in the trench 2, and thus form a lamellar-shape self-assembly structure in which two domains A and B, which are chemically different from each other, are alternately formed in a line shape.

The shape of the trench on the surface of the substrate may be determined by a pattern to be formed on the substrate or a self-assembly structure of the block copolymer, which is required depending on the pattern.

In one embodiment, the ratio (D/H) of a distance (D) of the mesa structures disposed apart to form the trench to a height (H) of the mesa structure may be in a range of 0.1 to 10, 0.5 to 10, 1 to 10, 1 to 9, 1 to 8, 1 to 7, 1 to 6, 1 to 5 or 1 to 4. Also, the ratio (D/W) of the distance (D) between the mesa structures and a width (W) of the mesa structure may be in a range of 0.5 to 10, 1 to 10, 1 to 9, 1 to 8, 1 to 7, 1 to 6, 1 to 5 or 1 to 4. The ratio (D/H or D/W) may be changed depending on a desired use. The term "distance (D) of the mesa structure" used herein refers to the shortest distance between adjacent mesa structures that are spaced apart, and the distance (D) may be, for example, about 10 to 500 nm, 10 to 450 nm, 10 to 400 nm, 10 to 350 nm, 10 to 300 nm, 50 to 300 nm, or 100 to 300 nm. The term "height (H) of the mesa structure" used herein is a dimension of the mesa structure measured upward from a surface of the substrate along a normal line direction of the substrate surface, and may be, for example, about 1 to 100 nm, 1 to 90 nm, 5 to 90 nm, 10 to 90 nm, 10 to 80 nm, or 20 to 70 nm. The term "width (W) of the mesa structure" used herein is a dimension of the mesa structure from the substrate surface along a vertical direction to the normal line direction of the substrate surface, and may be, for example, about 10 to 500 nm, 10 to 450 nm, 10 to 400 nm, 10 to 350 nm, 10 to 300 nm, 50 to 300 nm, or 100 to 300 nm.

For example, when the directed self-assembly material is a block copolymer, and a lamellar pattern of the block copolymer, the distance between the mesa structures may be about 1 to 20 L. In this case, a thickness of a film including the block copolymer, that is, a film formed in the trench may be about 1 to 10 L or 1 to 8 L. Here, L may refer to a pitch of the lamellar pattern formed by the block copolymer.

When the mesa structure is controlled in the above-described shape, self-assembly of the block copolymer may be effectively guided in the trench formed by the mesa structures. However, the dimension of the mesa structure is merely an example of the present application, and may be changed depending on a specific aspect.

A method of forming the above-described mesa structure on the substrate is not particularly limited, and thus a known method can be applied. For example, the mesa structure may be formed by etching the substrate by a suitable method, or depositing a suitable material on the substrate.

For example, the trench formed by the mesa structure may include sequentially forming a mesa structure-forming material layer, an antireflection layer, and a resist layer on the substrate; patterning the resist layer; and etching mesa structure-forming material layer using the patterned resist layer as a mask.

Here, the type of the mesa structure forming material is not particularly limited. For example, as will be described below, the material layer form a mesa structure through an etching process using the patterned resist layer as a mask, and in this process, a suitably etchable material may be used. For example, the material may be $SiO_2$, an amorphous carbon layer (ACL), a spin-on-glass (SOG), spin-on-carbon (SOC) or silicon nitride. Such a material layer may be coated by, for example, spin coating or deposition method such as chemical vapor deposition (CVD). A thickness of the material layer when the layer is formed is not particularly limited, and the layer may be formed to a suitable thickness by considering the height (H) of a desired mesa structure.

The antireflection layer may be formed on the mesa structure-forming material layer. The antireflection layer may be formed in siARC using a silicon (Si) material, and other than this, any known material may be used. The antireflection layer may be formed by a known coating or deposition method.

The resist layer may be formed on the antireflection layer. The resist layer may be formed using a known material, for example, a known material which can be patterned by a lithographic process. Such a resist layer may be patterned by a known lithographic process, and the patterned resist layer obtained thereby may be used as a mask in the following mesa forming process. The patterning of the resist layer may be performed to control the dimensions of the mesa structure at a desired level in the following etching process.

After the patterning of the resist layer, the etching process using the patterned resist layer as an etch mask, and in the etching process, the antireflection layer and the mesa-forming material layer in a region excluding a region protected by the etch mask may be etched. Such etching may be performed by a known etching process, and may be performed by, for example, a reactive ion etching (RIE) method. The above-described mesa structure is formed by the etching process, thereby forming a trench. The etching process may be performed until the mesa-forming material in the region not protected by the etch mask will be completely removed, or performed for some of the material to remain. Therefore, the trench may be formed by a side wall of the mesa structure and a surface of the substrate between the side walls, and may be formed on the side wall of the mesa structure and a surface of the mesa structure-forming material between the side walls.

According to the above description, one mesa-forming material layer and one antireflection layer are formed on the surface of the substrate, and the lithographic process is performed thereon. However, when necessary, two or more each of the mesa-forming material layers and antireflection layers may be alternately formed.

The self-assembly structure formed in the trench as described above may include vertically-oriented block copolymers. The term "vertical oriented" used herein may refer to an orientation property of a block copolymer and may refer to a case where an orientation direction of a self assembled structure formed by the block copolymer is vertical to a direction of a substrate. For example, the vertical oriented structure may refer to a case where block domains of the self assembled block copolymer lay side by side on the surface of the substrate and an interfacial region between the block domains is formed to be substantially vertical to the surface of the substrate. The term "vertical" used herein is an expression allowing for an error, for example, an error within ±10, ±8, ±6, ±4 or ±2 degrees.

The self-assembly structure of the block copolymer formed in the trench may be, for example, a spherical, cylindrical, gyroid or lamellar shape, and in one embodiment, a lamellar structure. However, the present application is not limited thereto. For example, when a block copolymer including first and second blocks is used as the block copolymer, in a segment of the first or second block or a third block covalently bonded thereto, another segment may have a regular structure such as a lamellar or cylindrical shape.

The surface within the trench, on which the layer of the block copolymer is formed, may be a surface to which conventional treatment that has been performed in order to realize the vertical orientation, such as a so called neutral surface treatment or a chemical pre-patterning, is not performed. Therefore, the surface within the trench, with which the layer comprising the block copolymer contacts, may be a surface to which any neutral treatment is not performed. The term "neutral treatment" may be translated as including any conventional treatment performed in order to realize the vertical orientation such as the neutral brush layer or the chemical pre-patterning. Further, the term "one layer contacting with another layer" as used herein may refer to a case there is no other layer between the two layers.

Further, in the above, a side wall of the mesa structure, with which the directed self assembly material such as the block copolymer contacts, may also be a surface to which any additional treatment is not performed. In conventional processes, in order to realize an appropriate self assembled structure, a treatment such as a hydrophobic or hydrophilic treatment is usually performed also on the side wall of the mesa structures, however, in the present method, such a treatment may not be performed.

In order to realize a vertically oriented or aligned self assembled structure in the layer contacting the surface within the trench and the side wall of the mesa structures, to which conventional treatment such as the neutral treatment that has been performed for realizing the vertical orientation is not performed, some factors may be controlled.

For example, as a block copolymer that is deposited within the trench, a block copolymer as described below may be used. The block copolymer as described below is capable of forming a vertical oriented or aligned structure even on the surface of the trench to which the neutral treatment is not performed.

The illustrative block copolymer used in the above method may include a first block and a second block different from the first block. Each block of the block copolymer may be formed only using one type of monomer, or two or more types of monomers. The block copolymer may be a diblock copolymer only including one first block and one second block. Alternatively, the block copolymer may be a triblock copolymer including each one of the first block and the second block, and additionally any one or all of the first and second blocks, or additionally a third block, other than the first and second blocks.

Since the block copolymer includes two or more polymer chains linked by covalent bonds, phase separation occurs, and thereby a self-assembly structure is formed. The inventors confirmed that, when a block copolymer satisfies any one or two or more conditions that will be described below, a vertically-oriented self-assembly structure can also be formed on a surface of the trench substrate on which the above-described neutral treatment is not performed. Therefore, another aspect of the present application provides a block copolymer satisfying at least one of the conditions that will be described below. The shape or size of the nano-scale structure may be controlled by controlling the size, for example, a molecular weight, of a block copolymer, or relative ratios between blocks. The following conditions are parallel, and thus one condition is not prior to another condition. The block copolymer may satisfy any one, or two or more selected from the following conditions. It was shown that the block copolymer can have vertical orientation through satisfaction of any one of the following conditions. The term "vertical orientation" used herein refers to the orientation of the block copolymer, and may refer to orientation of the nano structure formed by the block copolymer, which is vertical to a substrate direction. For example, the vertical orientation may mean that an interface between a domain formed by the first block and a domain formed by the second block of the block copolymer is vertical to a surface of the substrate. The term "vertical" used herein is an expression allowing for an error, which includes, for example, an error within ±10, ±8, ±6, ±4 or ±2 degrees.

Conventionally, the orientation of the nano structure is determined by which one of the blocks forming the block copolymer is exposed to the surface or in the air. Generally, since many substrates are polar, and the air is non-polar, among blocks of the block copolymer, a block having a higher polarity is in contact with the substrate, and a block having a smaller polarity is in contact with the air. Therefore, various techniques are suggested to be simultaneously in contact with blocks of the block copolymer, which have different characteristics, the most representative technique is the application of a neutral surface.

The inventor has confirmed that it becomes possible to realize the vertical orientation or vertical alignment even on the substrate to which any conventional treatment known for realizing the vertical orientation or alignment including the neutral brush layer is not performed by making the block copolymer to satisfy one, or two or more or all of the conditions as described below.

For example, a block copolymer according to one aspect of the present application may formed the vertical orientation with respect to both of hydrophilic and hydrophobic surfaces on which special pretreatment is not performed.

Also, in another aspect of the present application, the vertical orientation described above may be induced within a short time in a large area through thermal annealing.

One illustrative block copolymer in the present application includes a first block and a second block having a different chemical structure from the first block, and the block copolymer or the first block may show a peak at an azimuth angle within −90 to −70 degrees, and a peak at an azimuth angle within 70 to 90 degrees of a diffraction pattern of a scattering vector in a range of 12 nm$^{-1}$ to 16 nm$^{-1}$ of the grazing incident wide angle X ray scattering (GIWAXS) spectrum (Condition 1).

Another illustrative block copolymer used in the present application includes a first block and a second block having different chemical structure from the first block, and the block copolymer or the first block may show a melting transition peak or isotropic transition peak in a range of −80 to 200° C. through differential scanning calorimetry (DSC) analysis (Condition 2).

Another illustrative block copolymer used in the present application includes a first block and a second block having a different chemical structure from the first block, and the block copolymer or the first block may show a peak having a full width at half maximum (FWHM) in a range of 0.2 to 0.9 nm$^{-1}$ within the range of a scattering vector (q) of 0.5 to 10 nm$^{-1}$ through XRD analysis (Condition 3).

Another illustrative block copolymer used in the present application includes a first block and a second block having a different chemical structure from the first block. The first block includes a side chain, and the number (n) of chain-forming atoms of the side chain and the scattering vector (q) estimated by XRD analysis performed on the first block may satisfy the following Equation 2 (Condition 4).

$$3 \text{ nm}^{-1} \text{ to } 5 \text{ nm}^{-1} = nq/(2 \times \pi) \quad [\text{Equation 2}]$$

In Equation 2, n is the number of chain-forming atoms of the side chain, q is the smallest scattering vector (q) showing a peak in X-ray diffraction analysis performed on a block including the side chain, or a scattering vector (q) showing the peak having the largest peak area.

Another illustrative block copolymer used in the present application includes a first block and a second block having a different chemical structure from the first block, and the absolute value of the difference in surface energy between the first block and the second block may be 10 mN/m or less (Condition 5).

Another illustrative bock copolymer used in the present application includes a first block and a second block having a different chemical structure from the first block, and the absolute value of the difference in density between the first and second blocks may be 0.25 g/cm$^3$ or more (Condition 6).

Another illustrative block copolymer used in the present application includes a first block and a second block having a different chemical structure from the first block, and a volume fraction of the first block may be in a range of 0.2 to 0.6, and a volume fraction of the second block may be in a range of 0.4 to 0.8 (Condition 8). Such a block copolymer may form a so called lamellar structure.

In the present application, a physical property that can be changed by a temperature such as a wetting angle or density is, unless particularly defined otherwise, a value measured at a room temperature. The term "room temperature" is a natural temperature, which is not increased or decreased, for example, about 10 to 30° C., specifically, about 25 or 23° C.

In the block copolymer, the first block may be a block including a side chain, which will be described below.

Hereinafter, the following conditions will be described in detail.

A. Condition 1

Any one block of a block copolymer of the present application may show peaks at both of an azimuthal angle in a range of −90 to −70 degrees and an azimuthal angle in a range of 70 to 90 degrees of a diffraction pattern of a scattering vector in a range of 12 nm$^{-1}$ to 16 nm$^{-1}$ of a GIWAXS spectrum. The blocks showing the peaks may be blocks including side chains, which will be described below. In the specification, the block including the side chain may be a first block. Here, the azimuthal angle is an azimuthal angle when an angle of the diffraction pattern in an upper direction (direction of out-of-plane diffraction) is 0 degrees, which is measured in a clock-wise direction. In other words, the angle measured in the clock-wise direction is represented by a positive number, and the angle measured in a counter clock-wise direction is represented by a negative number. An FWHM observed at each azimuthal angle may be in a range of 5 to 70 degrees. The FWHM may be, in another embodiment, 7, 9, 11, 13, 15, 17, 19, 21, 25, 30, 35, 40, 45 degrees or more. The FWHM may be, in another embodiment, 65 or 60 degrees or less. A method of obtaining the GIWAXS spectrum is not particularly limited, and may be obtained by the following method of describing examples. A profile of a diffraction pattern peak of the obtained spectrum may be fitted through Gauss fitting, and therefrom, the FWHM may be obtained. In this case, when a half of the Gauss fitting result is obtained, the FWHM may be defined twice a value obtained from the result in which the half of the Gauss fitting result. In the Gauss fitting, a R square is in a range of about 0.26 to 0.95. That is, the above-described FWHM is observed at any one R square in the above range. A method of obtaining the above-described information is known in the art, and for example, a numerical analysis program such as Origin may be applied.

GIWAXS may be detected on a polymer prepared only using a monomer constituting a block to be detected. For example, the GIWAXS may be detected by forming a film using the polymer and performing thermal annealing on the film. The film may be formed by applying a coating solution prepared by diluting the polymer with a solvent (for example, fluorobenzene) at a concentration of about 0.7 wt % to have a thickness of about 25 nm and a coating area of 2.25 cm$^2$ (width: 1.5 cm, length: 1.5 cm), and thermally annealing such a coating film. The thermal annealing may be performed by maintaining the film, for example, at about 160° C. for about 1 hour. The block showing the above-described peak at the above-described azimuthal angle of the GIWAXS may be arranged to have orientation, and such a block may show an excellent phase separation or self-assembly characteristic, and vertical orientation with a different block.

B. Condition 2

The block copolymer of the present application or any one block of the block copolymer may show a melting transition peak or isotropic transition peak in a range of −80 to 200° C. through DSC analysis. When any one block of the block copolymer shows the above-described behavior in the DSC analysis, and the block copolymer including such a block simultaneously satisfies Conditions 2 and 3, the block showing the above behavior through the DSC analysis may be a block showing the peak in the GIWAXS described in Condition 2, that is, a peak showing at all of an azimuthal angle in a range of −90 to −70 degrees and an azimuthal angle in a range of 70 to 90 degrees of the diffraction pattern of a scattering vector in a range of 12 to 16 nm$^{-1}$ of the GIWAXS spectrum, for example, a first block. The block copolymer or any one block of the block copolymer may show any one or both of the melting transition peak and isotropic transition peak. Such a block copolymer may be a copolymer overall showing a crystal phase and/or liquid crystal phase, which are/is suitable for self-assembly, or showing such a crystal phase and/or liquid crystal phase.

The block copolymer showing the DSC behavior described above or any one block of the block copolymer may additionally satisfy the following condition in Condition 2.

For example, when the isotropic transition peak and the melting transition peak are simultaneously shown, the difference (Ti−Tm) between a temperature (Ti) at which the isotropic transition peak is shown and a temperature (Tm) at which the melting transition peak is shown may be in a range of 5 to 70° C. In another embodiment, the difference (Ti−Tm) may be 10° C. or more, 15° C. or more, 20° C. or more, 25° C. or more, 30° C. or more, 35° C. or more, 40° C. or more, 45° C. or more, 50° C. or more, 55° C. or more or 60° C. or more. The block copolymer or block copolymer including such a block having a difference (Ti−Tm) between the temperature (Ti) of the isotropic transition peak and the temperature (Tm) of the melting transition peak in the above range may have an excellent phase separation or self-assembly characteristic.

In another embodiment, when the isotropic transition peak and the melting transition peak are simultaneously shown, a ratio (M/I) of an area (I) of the isotropic transition peak and an area (M) of the melting transition peak may be in a range of 0.1 to 500. A block copolymer having the ratio (M/I) of the area (I) of the isotropic transition peak and the area (M) of the melting transition peak according to the DSC analysis or a block copolymer including such a block may maintain excellent phase separation or self-assembly characteristic. In another embodiment, the ratio (M/I) may be 0.5, 1, 1.5, 2, 2.5, 3 or more. Also, in another embodiment, the ratio (M/I) may be 450, 400, 350, 300, 250, 200, 150, 100, 90, 85 or less.

A method of performing the DSC analysis is known in the art, and in the present application, the analysis may be performed by such a known method.

A range of at temperature (Tm) at which the melting transition peak is shown may be in a range of −10° C. to 55° C. In another embodiment, the temperature (Tm) may be 50° C. or less, 45° C. or less, 40° C. or less, 35° C. or less, 30° C. or less, 25° C. or less, 20° C. or less, 15° C. or less, 10° C. or less, 5° C. or less, 0° C. or less.

The block copolymer may include a block having a side chain as will be described below. In this case, the block copolymer may satisfy the following Equation 1.

$$10° \text{C.} \leq Tm - 12.25° \text{C.} \times n + 149.5° \text{C.} \leq 10° \text{C.} \quad \text{[Equation 1]}$$

In Equation 1, Tm may be the temperature at which the melting transition peak of the block copolymer or block having a side chain, and n is the number of chain-forming atoms of the side chain.

The block copolymer satisfying the above equation may have an excellent phase separation or self-assembly characteristic.

In Equation 1, Tm−12.25° C.×n+149.5° C. may be, in another embodiment, about −8 to 8° C., about −6 to 6° C. or about −5 to 5° C.

C. Condition 3

The block copolymer of the present application may include a block showing at least one peak within a predetermined range of scattering vectors (q) in X-ray Diffraction analysis (XRD analysis). When the block copolymer satisfies Condition 3 as well as Conditions 1 and/or 2, the block satisfying Conditions 1 and/or 2 may be a block satisfying Condition 3. The block satisfying Condition 3 may be the first block.

For example, any one block of the block copolymer may show at least one peak within the scattering vector (q) of 0.5 to 10 nm$^{-1}$ in the XRD analysis. The scattering vector (q) shown by the peak may be, in another embodiment, 0.7, 0.9, 1.1, 1.3, 1.5 nm$^{-1}$ or more. The scattering vector (q) shown by the peak may be, in another embodiment, 9, 8, 7, 6, 5, 4, 3.5, 3 nm$^{-1}$ or less. An FWHM detected in the range of the scattering vector (q) may be in a range of 0.2 to 0.9 nm$^{-1}$. The FWHM may be, in another embodiment, 0.25, 0.3, 0.4 nm$^{-1}$ or more. The FWHM may be, in another embodiment, 0.85, 0.8, 0.75 nm$^{-1}$ or less.

In Condition 4, the term "full width at half maximum (FWHM)" may refer to a width (difference in scattering vector (q)) of a peak at a position showing ½ of the maximum peak intensity.

The scattering vector (q) and the FWHM in the XRD analysis is a value obtained by applying a numerical analysis method using a least square method on a result obtained by the following XRD analysis. In the above method, a part showing the least intensity in an XRD diffraction pattern may be set as a baseline to make the intensity 0, a profile of the XRD pattern peak is fitted by Gaussian fitting, and the scattering vector and the FWHM may be obtained from the fitted result. In the Gauss fitting, the R square is at least 0.9, 0.92, 0.94 or 0.96 or more. A method of obtaining such information from the XRD analysis is known in the art, and for example, a numerical analysis program such as Origin may be applied.

The block showing the FWHM in the range of the scattering vector (q) may include a crystal part suitable for self-assembly. The block copolymer including a block identified in the above-described range of the scattering vector (q) may have an excellent self-assembly characteristic.

The XRD analysis may be performed by measuring a scattering intensity according to a scattering vector after a sample was irradiated with x rays. The XRD analysis may be performed using a polymer prepared by polymerizing any one block of the block copolymer, for example, only a monomer constituting the first block. The XRD analysis may be performed on such a polymer without particular pretreatment, and for example, by irradiating the polymer with X rays after being dried under suitable conditions. As an X ray, an X ray having a vertical size of 0.023 mm and a horizontal size of 0.3 mm may be applied. An image of a 2D diffraction pattern may be obtained by scattering a sample using a measuring device (for example, 2D marCCD), and the obtained diffraction pattern may be fitted by the above-described method, thereby obtaining a scattering vector and an FWHM.

D. Condition 4

The block copolymer of the present application may include a block having a side chain, which will be described blow, as a first block, and the number (n) of chain-forming atoms of the side chain may satisfy the scattering vector (q) obtained by XRD analysis performed as shown in Condition 3 and the following Equation 2.

$$3 \text{ nm}^{-1} \text{ to } 5 \text{ nm}^{-1} = nq/(2\times\pi) \quad \text{[Equation 2]}$$

In Equation 2, n is the number of chain-forming atoms, and q is the least scattering vector (q) showing a peak in the XRD analysis performed on the block including a side chain, or a scattering vector (q) showing a peak having the largest peak area. Also, in Equation 2, π is the circular constant.

The scattering vector introduced to Equation 2 is a value obtained by the same method described in the XRD analysis method.

The scattering vector (q) introduced to Equation 2 may be, for example, in a range of 0.5 to 10 $nm^{-1}$. The scattering vector (q) introduced to Equation 2 may be, in another embodiment, 0.7 $nm^{-1}$ or more, 0.9 $nm^{-1}$ or more, 1.1 $nm^{-1}$ or more, 1.3 $nm^{-1}$ or more, 1.5 $nm^{-1}$ or more. The scattering vector (q) introduced to Equation 2 may be, in another embodiment, 9 $nm^{-1}$ or less, 8 $nm^{-1}$ or less, 7 $nm^{-1}$ or less, 6 $nm^{-1}$ or less, 5 $nm^{-1}$ or less, 4 $nm^{-1}$ or less, 3.5 $nm^{-1}$ or less, 3 $nm^{-1}$ or less.

Equation 2 shows the relation between the distance (D) between polymer main chain including the side chain and the number of chain-forming atoms when a film is formed of a polymer constituting only a block having the side chain of the block copolymer, and when the number of chain-forming atoms of the side chain of the polymer having the side chain satisfies Equation 2, crystallinity of the side chain is increased, and thus a phase separation characteristic or vertical orientation of the block copolymer may be highly enhanced. The nq/(2×π) according to Equation 2 may be, in another embodiment, 4.5 $nm^{-1}$ or less. Here, the distance between main chains of the polymer having the side chain (D, unit: nm) may be calculated by Equation D=2×π/q, in which D is the distance (D, unit: nm), and π and q are defined in Equation 2.

E. Condition 5

The absolute value of the difference in surface energy between the first block and the second block of the block copolymer of the present application may be 10, 9, 8, 7.5, 7 mN/m or less. The absolute value of the difference in surface energy may be 1.5, 2, 2.5 mN/m or more. A structure in which the first block and the second block having the above range of the absolute value of the difference in surface energy are linked by covalent bonds may direct effective microphase separation by phase separation caused by suitable non-compatibility. Here, the first block may be, for example, a block having a side chain which will be described above, or a block having an aromatic structure without a halogen atom.

The surface energy may be measured using a drop-shape analyzer (DSA100, KRUSS). Particularly, the surface energy may be measured on a film prepared by applying a coating solution prepared by diluting a target sample (a block copolymer or a homopolymer) for measuring surface energy with fluorobenzene at a concentration of a solid content of about 2 wt % onto a substrate to have a thickness of about 50 nm and a coating area of 4 $cm^2$ (width: 2 cm, length: 2 cm), drying the substrate at room temperature for about 1 hour, and thermal-annealing the dried substrate at 160° C. for about 1 hour. A process of measuring a contact angle by dropping deionized water whose surface tension is known onto the thermal-annealed film is repeated five times, thereby obtaining a mean value of the obtained five contact angles, and a process of obtaining a contact angle by dropping diiodomethane whose surface tension is known in the same manner as describe above is repeated five times, thereby obtaining a mean value of the obtained five contact angles. Afterward, surface energy may be obtained by substituting a value for surface tension (Strom value) of a solvent by the Owens-Wendt-Rabel-Kaelble method using a mean value of the obtained contact angles for the deionized water and diiodomethane, thereby obtaining surface energy. A value of the surface energy for each block of the block copolymer may be calculated on a homopolymer prepared only using a monomer forming the block.

When the block copolymer includes the above-described side chain, the block having the side chain may have higher surface energy than other blocks. For example, when the first block of the block copolymer includes a side chain, the first block may have higher surface energy than the second block. In this case, the surface energy of the first block may be in a range of about 20 to 40 mN/m. The surface energy of the first block may be 22, 24, 26, 28 mN/m or more. The surface energy of the first block may be 38, 36, 34, 32 mN/m or less. The block copolymer including the first block and having the different in surface energy as described above from the second block may have an excellent self-assembly characteristic.

F. Condition 6

The absolute value of a difference in density between the first block and the second block in the block copolymer may be 0.25 $g/cm^3$ or more, 0.3 $g/cm^3$ or more, 0.35 $g/cm^3$ or more, 0.4 $g/cm^3$ or more, or 0.45 $g/cm^3$ or more. The absolute value of the difference in density may be 0.9 $g/cm^3$ or less, 0.8 $g/cm^3$ or less, 0.7 $g/cm^3$ or less, 0.65 $g/cm^3$ or less, or 0.6 $g/cm^3$ or less. A structure in which the first block and the second block having the above range of the absolute value of the difference in density are linked by covalent bonds may direct effective microphase separation by phase separation caused by suitable non-compatibility.

The density of each block of the block copolymer may be measured using a known buoyancy method, and for example, the density may be measured by analyzing the mass of the block copolymer in a solvent having known mass and density in the air, such as ethanol.

When the above-described side chain is included, the block having the side chain may have a lower density than other blocks. For example, when the first block of the block copolymer includes the side chain, the first block may have a lower density than the second block. In this case, the density of the first block may be in a range of about 0.9 to 1.5 $g/cm^3$. The density of the first block may be 0.95 $g/cm^3$ or more. The density of the first block may be 1.4 $g/cm^3$ or less, 1.3 $g/cm^3$ or less, 1.2 $g/cm^3$ or less, 1.1 $g/cm^3$ or less, or 1.05 $g/cm^3$ or less. The block copolymer including the first block and having the difference in density from the second block may have an excellent self-assembly characteristic.

G. Condition 7

The block copolymer may include the first block having a volume fraction of 0.4 to 0.8, and the second block having a volume fraction of 0.2 to 0.6. When the block copolymer includes the side chain, the block having the chain may have a volume fraction of 0.4 to 0.8. For example, when the first block includes the chain, the first block may have a volume fraction of 0.4 to 0.8, and the second block may have a volume fraction of 0.2 to 0.6. The sum of the volume fractions of the first block and the second block may be 1. The block copolymer including the blocks having the above-described volume fractions may have excellent self-assembly. The volume fraction of each block of the block copolymer may be obtained based on a density and a molecular weight measured by gel permeation chromatography (GPC) of each block. Here, the density may be calculated by the above-described method.

As described above, the block copolymer may satisfy any one or two or more selected from Conditions 1 to 7.

For example, the block copolymer may be a block copolymer satisfying Condition 1, 2, 3, 4, 5, 6 or 7.

In one embodiment, the block copolymer may include a first block satisfying one, or two or more of Conditions 1 to 4 among the above described conditions, and a second block having a difference in surface energy according to Condition 5.

In another embodiment, the block copolymer may include a first block satisfying one, or two or more of Conditions 1 to 4 among the above described conditions, and a second having a difference in surface energy according to Condition 5, and therefore a ratio of the first block to the second block may satisfy Condition 7.

While not limited by a theory, the first block satisfying any one of Conditions 1 to 4 may have crystallinity or liquid crystallinity, and therefore, may be packed to have regularity in the formation of a self-assembly structure. In this state, when the first block and the second block satisfy a difference in surface energy according to Condition 5, domains formed by each of the first and second blocks may be substantially neutralized, and therefore, the film may be vertically oriented regardless of the characteristics of a surface on which the self-assembled film is formed. When the ratio of the blocks satisfies Condition 7, the neutralization effect may be maximized, and therefore the resin orientation effect may be maximized As another condition, a number average molecular weight (Mn) of the block copolymer may be, for example, in a range of 3,000 to 300,000. The term "number average molecular weight" is a conversion value with respect to standard polystyrene measured by gel permeation chromatography (GPC), and the term "molecular weight" used herein means, unless particularly defined otherwise, the number average molecular weight (Mn). The molecular weight (Mn) may be, in another embodiment, for example, 3000 or more, 5000 or more, 7000 or more, 9000 or more, 11000 or more, 13000 or more, or 15000 or more. The molecular weight (Mn) may be, in still another embodiment, about 250000 or less, 200000 or less, 180000 or less, 160000 or less, 140000 or less, 120000 or less, 100000 or less, 90000 or less, 80000 or less, 70000 or less, 60000 or less, 50000 or less, 40000 or less, 30000 or less, or 25000 or less. The block copolymer may have a polydispersity (Mw/Mn) in a range of 1.01 to 1.60. The polydispersity may be, in another embodiment, about 1.1 or more, 1.2 or more, 1.3 or more, or 1.4 or more.

In such a range, the block copolymer may have a suitable self-assembly characteristic. The number average molecular weight of the block copolymer may be controlled by considering a desired self-assembly structure.

The above-described conditions may be satisfied by, for example, control of the structure of the block copolymer. For example, at least one or all of the first and second blocks satisfying one or more of the above-described conditions may at least include an aromatic structure. All of the first block and the second block may include an aromatic structure, and in this case, the aromatic structure included in the first and second blocks may be the same as or different from each other. Also, at least one of the first and second blocks of the block copolymer satisfying one or more of the above-described conditions may include the above-described side chain, or at least one halogen atom, which will be described below, and the side chain and the halogen atom may be substituted by the aromatic structure. The block copolymer of the present application may include two or more blocks.

As described above, the first and/or second block(s) of the block copolymer may include an aromatic structure. Such an aromatic structure may be included in only one or both of the first and second blocks. When both of the blocks include aromatic structures, the aromatic structures of the blocks may be the same as or different from each other.

The term "aromatic structure" used herein refers to the structure of an aromatic compound, and the term "aryl group" may refer to a monovalent residue derived from the aromatic compound, and "arylene group" may refer to a bivalent residue derived from the aromatic compound. Here, the aromatic compound is, unless particularly defined otherwise, a compound which has a benzene ring, or two or more benzene rings, which are linked by sharing one or two carbon atoms or with an optional linker, or a derivative thereof. Therefore, the aryl group, that is, the monovalent residue derived from the aromatic compound may refer to a substituent in which a radical formed by releasing one hydrogen atom of the aromatic compound forms a covalent bond, and the arylene group, that is, the bivalent residue derived from the aromatic compound may refer to a substituent in which a radical formed by releasing two hydrogen atoms of the aromatic compound forms a covalent bond. The aryl group or arylene group may be, for example, an aryl group or arylene group having 6 to 30, 6 to 25, 6 to 21, 6 to 18, or 6 to 13 carbon atoms. As the aryl group or arylene group, a monovalent or bivalent residue derived from benzene, naphthalene, azobenzene, anthracene, phenanthrene, tetracene, pyrene or benzopyrene may also be used. The term "aromatic structure" used herein may used as the same meaning as the aryl group or arylene group.

The aromatic structure may be a structure included in the block main chain or a structure linked to the block main chain as a side chain. The above-described conditions can be adjusted by suitable control of the aromatic structure which can be included in each block.

In one embodiment, the block copolymer satisfying at least one of the conditions may include a first block including a side chain and a second block different from the first block. Here, the side chain may be a side chain having 8 or more chain-forming atoms, which will be described below. The first block may be a block satisfying any one, two or more, or all of Conditions 2, 3, 4 and 5.

The first block may include a ring structure, and the side chain may be substituted in the ring structure. The ring structure may be the above-described aromatic structure, an aryl or arylene group, or an alicyclic ring structure. Such a ring structure may be a ring structure without having a halogen atom.

The "alicyclic ring structure" used herein refers to, unless particularly defined otherwise, a cyclic hydrocarbon structure, not an aromatic ring structure. The alicyclic ring structure may be included in the block copolymer in the form of a monovalent or bivalent residue. The alicyclic ring structure may be, unless particularly defined otherwise, for example, an alicyclic ring structure having 3 to 30, 3 to 25, 3 to 21, 3 to 18, or 3 to 13 carbon atoms.

The second block included along with the first block is a block, which is chemically different from the first block. The second block may be, for example, a block including a halogen atom, for example, a chlorine atom or fluorine atom. The second block may include 1, 2, 3, 4, 5 or more halogen atoms. The number of halogen atoms may be, for example, 30, 25, 20, 15, 10, 9, 8, 7, 6, 5 or less. The second block may include a ring structure, and the halogen atom may be substituted in such a ring structure. The ring structure may be the above-described aromatic structure, aryl or arylene group.

The term "side chain" used herein means a chain linked to the main chain of a polymer, and the term "chain-forming atom" means an atom forming a linear structure of the chain as an atom forming the side chain. The side chain may be linear or branched, but the number of chain-forming atoms may be calculated only as the number of atoms constituting the longest linear chain, not including another atom binding to the chain-forming atom (for example, when the chain-forming atom is a carbon atom, a hydrogen atom binding to the carbon atom). For example, in the case of a branched chain, the number of chain-forming atoms may be calculated as the number of chain-forming atoms constituting the longest chain. For example, when the side chain is n-pentyl group, all of the chain-forming atoms are carbons, the number of which is 5, and even when the side chain is 2-methylpentyl group, all of the chain-forming atoms are carbon, the number of which is 5. As the chain-forming atom, carbon, oxygen, sulfur or nitrogen may be used, and a suitable chain-forming atom may be carbon, oxygen or nitrogen, or carbon or oxygen. The number of chain-forming atoms may be 8 or more, 9 or more, 10 or more, 11 or more, or 12 or more. The number of chain-forming atoms may also, 30 or less, 25 or less, 20 or less, or 16 or less.

To control the above-described condition, a chain having 8 or more chain-forming atoms may be linked to a side chain of the first block of the block copolymer. The terms "chain" and "side chain" used herein may refer to the same subjects.

The side chain may be, as described above, a chain having 8 or more, 9 or more, 10 or more, 11 or more, or 12 or more chain-forming atoms. The number of chain-forming atoms may also be 30 or less, 25 or less, 20 or less, or 16 or less. The chain-forming atom may be a carbon, oxygen, nitrogen or sulfur atom, and preferably, carbon or oxygen.

As a side chain, a hydrocarbon chain such as an alkyl group, an alkenyl group or an alkynyl group may be used. At least one of the carbon atoms of the hydrocarbon chain may be substituted with a sulfur atom, an oxygen atom or a nitrogen atom.

When the side chain is linked to a ring structure such as an aromatic structure, the chain may be directly linked to the ring structure, or linked by means of a linker. As the linker, an oxygen atom, a sulfur atom, $-NR_1-$, $-S(=O)_2-$, a carbonyl group, an alkylene group, an alkenylene group, an alkynylene group, $-C(=O)-X_1-$ or $-X_1-C(=O)-$ may be used. Here, $R_1$ is a hydrogen, an alkyl group, an alkenyl group, an alkynyl group, an alkoxy group or an aryl group, $X_1$ is a single bond, an oxygen atom, a sulfur atom, $-NR_2-$, $-S(=O)_2-$, an alkylene group, an alkenylene group or an alkynylene group, and here, $R_2$ may be a hydrogen, an alkyl group, an alkenyl group, an alkynyl group, an alkoxy group or an aryl group. As a suitable linker, an oxygen atom may be used. The side chain may be linked to a ring structure such as an aromatic structure, for example, by means of an oxygen atom or nitrogen atom.

When the above-described ring structure such as an aromatic structure is linked to the main chain of the block as a side chain, the aromatic structure may also be directly linked or may be linked to the main chain by means of a linker. In this case, as a linker, an oxygen atom, a sulfur atom, $-S(=O)_2-$, a carbonyl group, an alkylene group, an alkenylene group, an alkynylene group, $-C(=O)-X_1-$ or $-X_1-C(=O)-$ may be used, and in this case, $X_1$ is a single bond, an oxygen atom, a sulfur atom, $-S(=O)_2-$, an alkylene group, an alkenylene group or an alkynylene group. As a suitable linker linking the aromatic structure to the main chain, $-C(=O)-O-$ or $-O-C(=O)-$ may be used, but the present application is not limited thereto.

In another embodiment, the aromatic structure included in the first and/or second block(s) of the block copolymer may include 1, 2, 3, 4, 5 or more halogen atoms. The number of halogen atoms may be, for example, 30, 25, 20, 15, 10 or less. As the halogen atom, fluorine or chlorine may be used, and the fluorine atom is preferably used. As described above, the block having the aromatic structure including the halogen atom may efficiently implement a phase-separated structure through a suitable interaction with other blocks.

As the aromatic structure including a halogen atom, an aromatic structure having 6 to 30, 6 to 25, 6 to 21, 6 to 18, or 6 to 13 carbon atoms may be used, but the present application is not limited thereto.

In the block copolymer, all of the first and second blocks include aromatic structures, in order to implement a suitable phase-separated structure, the first block may include an aromatic structure without including a halogen atom, and the second block may include an aromatic structure including a halogen atom. Also, the above-described side chain may be directly linked or linked by means of a linker including oxygen or nitrogen to the aromatic structure of the first block.

When the block copolymer includes a block having a side chain, the block may be, for example, a block including the unit represented by Formula 1. The block may be a block including the following unit of Formula 1 as a main component. The expression "a block includes a unit as a main component" used herein may mean that the block includes the unit at 60, 70, 80, 90, 95% or more based on a weight, or 60, 70, 80, 90, 95 mol % or more.

[Formula 1]

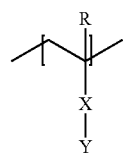

In Formula 1, R is a hydrogen or an alkyl group, X is a single bond, an oxygen atom, a sulfur atom, $-S(=O)_2-$, a carbonyl group, an alkylene group, an alkenylene group, an alkynylene group, $-C(=O)-X_1-$ or $-X_1-C(=O)-$, and in this case, $X_1$ is an oxygen atom, a sulfur atom, $-S(=O)_2-$, an alkylene group, an alkenylene group or an alkynylene group, and Y is a monovalent substituent including a ring structure to which the side chain having a chain-forming atom is linked.

In Formula 1, Y is a substituent including at least a ring structure. For example, when the ring structure is an aromatic ring, the number of chain-forming atoms may be 3 or more, and when the ring structure is an alicyclic ring structure, the number of chain-forming atoms may be 8 or more. Even when the ring structure is an aromatic ring structure, the number of chain-forming atoms may be 5, 7, 8 or more.

In Formula 1, X may be, in another embodiment, a single bond, an oxygen atom, a carbonyl group, —C(=O)—O— or —O—C(=O)—, and preferably —C(=O)—O—, but the present application is not limited thereto.

In Formula 1, the monovalent substituent of Y includes a chain structure formed of at least 3 or 8 chain-forming atoms.

As described above, the term "chain-forming atom" used herein refers to a predetermined chain, for example, an atom forming a linear structure of a side chain. The chain may be linear or branched, but the number of chain-forming atoms is calculated only as the number of atoms constituting the longest linear chain. A different atom binding to the chain-forming atom (for example, when the chain-forming atom is a carbon atom, a hydrogen atom binding to the carbon atom) is not calculated. Also, in the case of a branched chain, the number of chain-forming atoms may be calculated as the number of chain-forming atoms constituting the longest chain. For example, when the chain is an n-pentyl group, the chain-forming atoms are all carbons, the number of which is 5, and even when the chain is a 2-methylpentyl group, the chain-forming atoms are all carbons, the number of which is 5. As the chain-forming atom, carbon, oxygen, sulfur or nitrogen may be used, and a suitable chain-forming atom may be carbon, oxygen or nitrogen, or carbon or oxygen. The number of chain-forming atoms may be 3 or more, 5 or more, 7 or more, 8 or more, 9 or more, 10 or more, 11 or more, or 12 or more. The number of chain-forming atoms may also be 30 or less, 25 or less, 20 or less, or 16 or less. The suitable lower limit of the number of chain-forming atoms may be determined by the type of a ring structure as described above.

The block of Formula 1 may allow the block copolymer to have an excellent self-assembly characteristic and to satisfy the above condition.

In one embodiment, the chain may be a linear hydrocarbon chain such as a linear alkyl group. In this case, the alkyl group may be an alkyl group having 3, 5, 7, 8 or more, 8 to 30, 8 to 25, 8 to 20, or 8 to 16 carbon atoms. One or more carbon atoms of the alkyl group may be optionally substituted with an oxygen atom, and at least one hydrogen atom of the alkyl group may be optionally substituted with another substituent.

In Formula 1, Y includes a ring structure, and the chain may be linked to the ring structure. Due to such a ring structure, the self-assembly characteristic of the block copolymer may be further improved. The ring structure may be an aromatic structure, or an alicyclic structure.

The chain may be directly linked, or linked by means of a linker to the ring structure. As the linker, an oxygen atom, a sulfur atom, —NR$_1$—, —S(=O)$_2$—, a carbonyl group, an alkylene group, an alkenylene group, an alkynylene group, —C(=O)—X$_1$— or —X$_1$—C(=O)— may be used, and in this case, R$_1$ may be a hydrogen, an alkyl group, an alkenyl group, an alkynyl group, an alkoxy group or an aryl group, X$_1$ may be a single bond, an oxygen atom, a sulfur atom, —NR$_2$—, —S(=O)$_2$—, an alkylene group, an alkenylene group or an alkynylene group, in which R$_2$ may be a hydrogen, an alkyl group, an alkenyl group, an alkynyl group, an alkoxy group or an aryl group. As a suitable linker, an oxygen atom or a nitrogen atom may be used. The chain may be linked to the aromatic structure, for example, by means of an oxygen atom or a nitrogen atom. In this case, the linker may be an oxygen atom, or NR$_1$— (in which R$_1$ is a hydrogen, an alkyl group, an alkenyl group, an alkynyl group, an alkoxy group or an aryl group).

The Y in Formula 1 may be presented by Formula 2.

—P-Q-Z [Formula 2]

In Formula 2, P is an arylene group or a cycloalkylene group, Q is a single bond, an oxygen atom or —NR$_3$—, wherein R$_3$ is a hydrogen, an alkyl group, an alkenyl group, an alkynyl group, an alkoxy group or an aryl group, Z is the chain having three or more chain-forming atoms when P is an arylene group, or the chain having 8 or more chain-forming atoms when P is a cycloalkylene group. When Y in Formula 1 is the substituent of Formula 2, P of Formula 2 may be directly linked to X of Formula 1.

In Formula 2, as a suitable example, P may be an arylene group having 6 to 12 carbon atoms, and for example, a phenoylene group, but the present application is not limited thereto.

In Formula 2, as a suitable example, Q may be an oxygen atom or —NR$_1$— (wherein R$_1$ is a hydrogen, an alkyl group, an alkenyl group, an alkynyl group, an alkoxy group or an aryl group).

As an example of the unit of Formula 1 (hereinafter, may be referred to as a unit of the first block), the unit represented by Formula 3. Such a block may be referred to as a 1A block unit in the specification, but the present application is not limited thereto.

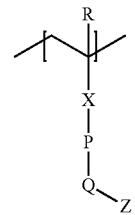

[Formula 3]

In Formula 3, R is a hydrogen or an alkyl group having 1 to 4 carbon atoms, X is a single bond, an oxygen atom, —C(=O)—O— or —O—C(=O)—, P is an arylene group, Q is an oxygen atom or —NR$_3$—, wherein R$_3$ is a hydrogen, an alkyl group, an alkenyl group, an alkynyl group, an alkoxy group or an aryl group, and Z is a linear chain having 8 or more chain-forming atoms. In another embodiment, in Formula 3, Q may be an oxygen atom.

In another embodiment, the unit of the first block may be represented by Formula 4. Such a unit may be called a 1B block unit in the specification.

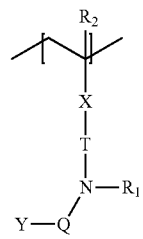

[Formula 4]

In Formula 4, R$_1$ and R$_2$ are each independently a hydrogen or an alkyl group having 1 to 4 carbon atoms, X is a single bond, an oxygen atom, a sulfur atom, —S(=O)$_2$—, a carbonyl group, an alkylene group, an alkenylene group, an alkynylene group, —C(=O)—X$_1$— or —X$_1$—C(=O)—, wherein X$_1$ is a single bond, an oxygen atom, a sulfur atom, —S(=O)$_2$—, an alkylene group, an alkenylene group or an alkynylene group, T is a single bond or an arylene group, Q is a single bond or a carbonyl group, and Y is a chain having 8 or more chain-forming atoms.

In the 1B block unit represented by Formula 4, X may be a single bond, an oxygen atom, a carbonyl group, —C(=O)—O— or —O—C(=O)—.

Specifically, as the chain of Y included in the 1B block unit, a similar one described in Formula 1 may be applied.

In another embodiment, the first block unit may be, in any one of Formulas 1, 3 and 4, a unit in which at least one chain-forming atom of the chain having 8 or more chain-forming atoms has an electronegativity of 3 or higher. The electronegativity of the atom may be, in another embodiment, 3.7 or less. In the specification, the unit may be referred to as a 1C block unit. Here, as an atom with an electronegativity of 3 or more, a nitrogen atom or an oxygen atom may be used, but the present application is not limited thereto.

The type of another block (hereinafter, may be referred to as a second block), which may be included in the block copolymer with the first block including the 1A, 1B or 1C block units, is not particularly limited.

For example, the second block may be a polyvinylpyrrolidone block, a polylactic acid block, a polyvinylpyrridine block, a polystyrene block such as poylstyrene or poly trimethylsilylstyrene, a polyalkylene oxide block such as polyethylene oxide, a polybutadiene block, a polyisoprene block, or a polyolefin block such as polyethylene. Such a block may be referred to as a 2A block in the specification.

In one embodiment, as the second block which may be included with the first block including the 1A, 1B or 1C block unit, a block having an aromatic structure including at least one halogen atom may be used.

Such a second block may be, for example, a block including the unit represented by Formula 5. The unit of Formula 5 may be referred to as a 2B block unit in the specification. The second block may include the 2B block unit as a main component.

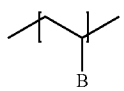

[Formula 5]

In Formula 5, B is a monovalent substituent having an aromatic structure including one or more halogen atoms.

The second block including such a unit may be excellently interacted with the first block for the block copolymer to have an excellent self-assembly characteristic.

In Formula 5, the aromatic structure may be, for example, an aromatic structure having 6 to 18 or 6 to 12 carbon atoms.

In addition, as the halogen atom included in Formula 5, a fluorine atom or a chlorine atom may be used, and suitably a fluorine atom may be used, but the present application is not limited thereto.

In one embodiment, B of Formula 5 may be a monovalent substituent having an aromatic structure having 6 to 12 carbon atoms, which is substituted with 1, 2, 3, 4, 5 or more halogen atoms. Here, the upper limit of the number of halogen atoms is not particularly limited, and therefore, for example, 10, 9, 8, 7, 6 or less halogen atoms may be included.

For example, the 2B block unit of Formula 5 may be represented by Formula 6.

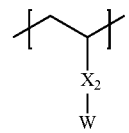

[Formula 6]

In Formula 6, X$_2$ is a single bond, an oxygen atom, a sulfur atom, —S(=O)$_2$—, an alkylene group, an alkenylene group, an alkynylene group, —C(=O)—X$_1$— or —X$_1$—C(=O)—, wherein X$_1$ is a single bond, an oxygen atom, a sulfur atom, —S(=O)$_2$—, an alkylene group, an alkenylene group or an alkynylene group, and W is an aryl group including at least one halogen atom. Here, W may be an aryl group substituted with at least one halogen atom, for example, an aryl group having 6 to 12 carbon atoms substituted with 2, 3, 4, 5 or more halogen atoms.

The 2B block unit may be represented by, for example, Formula 7.

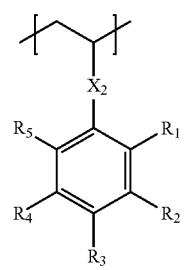

[Formula 7]

In Formula 7, X$_2$ is a single bond, an oxygen atom, a sulfur atom, —S(=O)$_2$—, an alkylene group, an alkenylene group, an alkynylene group, —C(=O)—X1- or —X1-C(=O)—, wherein X$_1$ is a single bond, an oxygen atom, a sulfur atom, —S(=O)2-, an alkenylene group, an alkenylene group or an alkynylene group, R$_1$ to R$_5$ may be each independently a hydrogen, an alkyl group, a haloalkyl group or a halogen atom, and the number of halogen atoms including R$_1$ to R$_5$ is 1 or more.

In Formula 7, X$_2$ may be, in another embodiment, a single bond, an oxygen atom, an alkylene group, —C(=O)—O— or —O—C(=O)—.

In Formula 7, R$_1$ to R$_5$ are each independently a hydrogen, an alkyl group, a haloalkyl group or a halogen atom, and may include 1 or more, 2 or more, 3 or more, 4 or more, or 5 or more halogen atoms, for example, fluorine atoms. The number of the halogen atoms, for example, the fluorine atoms, included in R$_1$ to R$_5$ may be 10 or less, 9 or less, 8 or less, 7 or less, or 6 or less.

In one embodiment, the second block may be a block including the unit represented by Formula 8. The unit of Formula 8 may be referred to as a 2C block unit in the specification. The second block may include the 2C block unit as a main component.

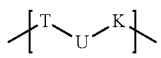
[Formula 8]

In Formula 8, T and K are each independently an oxygen atom or a single bond, and U is an alkylene group.

In one embodiment, the 2C block unit may be a block in which U in Formula 10 may be an alkylene group having 1 to 20, 1 to 16, 1 to 12, 1 to 8, or 1 to 4 carbon atoms.

The 2C block unit may be a block in which any one of T and K of Formula 8 may be a single bond, and the other one may be an oxygen atom. Such a block may be a block in which U is an alkylene group having 1 to 20, 1 to 16, 1 to 12, 1 to 8, or 1 to 4 carbon atoms.

The 2C block unit may be a block in which all of T and K of Formula 8 are oxygen atoms. Such a block may be a block in which U is an alkylene group having 1 to 20, 1 to 16, 1 to 12, 1 to 8, or 1 to 4 carbon atoms.

The second block may be, in another embodiment, a block including one or more metal atoms or metalloid atoms. Such a block may be referred to as a 2D block in the specification. Such a block may improve etch selectivity, for example, when an etching process is performed on the self-assembled film formed using the block copolymer.

As the metal or metalloid atom included in the 2D block, a silicon atom, an iron atom or a boron atom may be used, but any one that can show suitable etch selectivity caused by a difference from other atoms included in the block copolymer is used without particular limitation.

The 2D block may include 1, 2, 3, 4, 5 or more halogen atoms, for example, fluorine atoms, in addition to the metal or metalloid atom. The number of the halogen atoms such as fluorine atoms included in the 2D block may be 10, 9, 8, 7, 6 or less.

The 2D block may include the unit represented by Formula 9 (2D block unit). The 2D block may include the unit of Formula 9 as a main component.

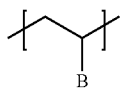
[Formula 9]

In Formula 9, B may be a monovalent substituent having a substituent including a metal atom or a metalloid atom and an aromatic structure including a halogen atom.

The aromatic structure of Formula 9 may be an aromatic structure having 6 to 12 carbon atoms, for example, an aryl group or an arylene group.

The 2D block unit of Formula 9 may be, for example, represented by Formula 10.

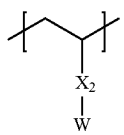
[Formula 10]

In Formula 10, $X_2$ is a single bond, an oxygen atom, a sulfur atom, $-NR_1-$, $-S(=O)_2-$, an alkylene group, an alkenylene group, an alkynylene group, $-C(=O)-X_1-$ or $-X_1-C(=O)-$, wherein $R_1$ is a hydrogen, an alkyl group, an alkenyl group, an alkynyl group, an alkoxy group or an aryl group, $X_1$ is a single bond, an oxygen atom, a sulfur atom, $-NR_2-$, $-S(=O)_2-$, an alkylene group, an alkenylene group or an alkynylene group, and W is an aryl group having a substituent including a metal atom or a metalloid atom and at least one halogen atom.

Here, W may be an aryl group having 6 to 12 carbon atoms, which has a substituent including a metal atom or a metalloid atom and at least one halogen atom.

In such an aryl group, at least 1 or 1 to 3 substituents including a metal atom or a metalloid atom may be included, and 1, 2, 3, 4, 5 or more halogen atoms may be included.

Here, 10 or less, 9 or less, 8 or less, 7 or less, or 6 or less halogen atoms may be included.

The 2D block unit of Formula 10 may be represented by, for example, Formula 11.

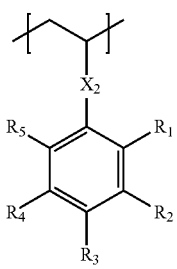
[Formula 11]

In Formula 11, $X_2$ a single bond, an oxygen atom, a sulfur atom, $-NR_1-$, $-S(=O)_2-$, an alkylene group, an alkenylene group, an alkynylene group, $-C(=O)-X_1-$ or $-X_1-C(=O)-$, wherein $R_1$ is a hydrogen, an alkyl group, an alkenyl group, an alkynyl group, an alkoxy group or an aryl group, $X_1$ is a single bond, an oxygen atom, a sulfur atom, $-NR_2-$, $-S(=O)_2-$, an alkylene group, an alkenylene group or an alkynylene group, $R_1$ to $R_5$ are each independently a hydrogen, an alkyl group, a haloalkyl group, a halogen atom, or a substituent including a metal or metalloid atom. At least one of $R_1$ to $R_5$ is a halogen atom, and at least one of $R_1$ to $R_5$ is a substituent including a metal or metalloid atom.

In Formula 11, at least 1, 1 to 3, or 1 to 2 of $R_1$ to $R_5$ may be substituents including above-described a metal or metalloid atom.

In Formula 11, in $R_1$ to $R_5$, 1, 2, 3, 4, 5 or more halogen atoms may be included. The number of halogen atoms included in $R_1$ to $R_5$ may be 10, 9, 8, 7, 6 or less.

As described above, as the substituent including a metal or metalloid atom, a trialkylsiloxy group, a ferrocenyl group, a silsesquioxanyl group such as a polyhedral oligomeric silsesquioxane group, or a carboranyl group may be used, and such a substituent may be any one selected to ensure etch selectivity, including at least one metal or metalloid atom, without particular limitation.

In another embodiment, the second block may be a block including an atom with an electronegativity of 3 or higher, not a halogen atom (hereinafter, may be referred to as a non-halogen atom). The block described above may be referred to as a 2E block in the specification. In another embodiment, the electronegativity of the non-halogen atom included in the 2E block may be 3.7 or less.

As the non-halogen atom included in the 2E block, a nitrogen atom or an oxygen atom may be used, but the present application is not limited thereto.

The 2E block may include 1, 2, 3, 4, 5 or more halogen atoms, for example, fluorine atoms, along with the non-halogen atom with an electronegativity of 3 or higher. The number of the halogen atoms such as the fluorine atoms included in the 2E block may be 10, 9, 8, 7, 6 or less.

The 2E block may include may include the unit represented by Formula 12 (the 2E block unit). The unit may be included in the 2E block as a main component.

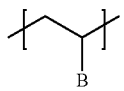

[Formula 12]

In Formula 12, B may be a monovalent substituent, which has a substituent including a non-halogen atom with an electronegativity of 3 or more and an aromatic structure including a halogen atom.

The aromatic structure of Formula 12 may be an aromatic structure having 6 to 12 carbon atoms, for example, an aryl group or an arylene group.

In another embodiment, the unit of Formula 12 may be represented by Formula 13.

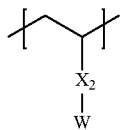

[Formula 13]

In Formula 13, $X_2$ is a single bond, an oxygen atom, a sulfur atom, $-NR_1-$, $-S(=O)_2-$, an alkylene group, an alkenylene group, an alkynylene group, $-C(=O)-X_1-$ or $-X_1-C(=O)-$, wherein $R_1$ is a hydrogen, an alkyl group, an alkenyl group, an alkynyl group, an alkoxy group or an aryl group, $X_1$ is a single bond, an oxygen atom, a sulfur atom, $-NR_2-$, $-S(=O)_2-$, an alkylene group, an alkenylene group or an alkynylene group, and W is an aryl group, which includes a substituent including a non-halogen atom with an electronegativity of 3 or more and at least one halogen atom.

Here, W may be an aryl group having 6 to 12 carbon atoms, which includes a substituent including a non-halogen atom with an electronegativity of 3 or more and at least one halogen atom.

In such an aryl group, the number of the substituents including a non-halogen atom with an electronegativity of 3 or more may be at least 1 or 1 to 3. Also, the number of the halogen atoms may be 1, 2, 3, 4, 5 or more. Here, the number of halogen atoms may be 10, 9, 8, 7, 6 or less.

In another embodiment, the unit of Formula 13 may be represented by Formula 14.

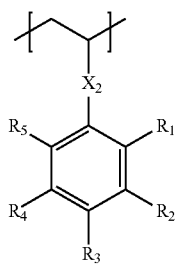

[Formula 14]

In Formula 14, $X_2$ is a single bond, an oxygen atom, a sulfur atom, $-NR_1-$, $-S(=O)_2-$, an alkylene group, an alkenylene group, an alkynylene group, $-C(=O)-X_1-$ or $-X_1-C(=O)-$, wherein $R_1$ is a hydrogen, an alkyl group, an alkenyl group, an alkynyl group, an alkoxy group or an aryl group, $X_1$ is a single bond, an oxygen atom, a sulfur atom, $-NR_2-$, $-S(=O)_2-$, an alkylene group, an alkenylene group or an alkynylene group, $R_1$ to $R_5$ are each independently a hydrogen, an alkyl group, a haloalkyl group, a halogen atom and a substituent including a non-halogen atom with an electronegativity of 3 or more. At least one of $R_1$ to $R_5$ is a halogen atom, and at least one of $R_1$ to $R_5$ is a substituent including a non-halogen atom with an electronegativity of 3 or more.

In Formula 14, at least 1, 1 to 3, or 1 to 2 of $R_1$ to $R_5$ may be the above-described substituents including a non-halogen atom with an electronegativity of 3 or more.

In Formula 14, $R_1$ to $R_5$ may include 1, 2, 3, 4, 5 or more halogen atoms. $R_1$ to $R_5$ may include 10, 9, 8, 7, 6 or less halogen atoms.

As described above, as the substituent including a non-halogen atom with an electronegativity of 3 or more, a hydroxyl group, an alkoxy group, a carboxyl group, an amido group, an ethylene oxide group, a nitrile group, a pyridine group, or an amino group, but the present application is not limited thereto.

In another embodiment, the second block may include an aromatic structure having a heterocyclic substituent. Such a second block may be referred to as a 2F block in the specification.

The 2F block may include the unit represented by Formula 15. The following unit may be included in the 2F block as a main component.

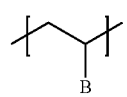

[Formula 15]

In Formula 15, B is a monovalent substituent having an aromatic structure having 6 to 12 carbon atoms, which is substituted with a heterocyclic substituent.

The aromatic structure of Formula 15 may include one or more halogen atom, when necessary.

The unit of Formula 15 may be represented by Formula 16.

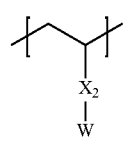

[Formula 16]

In Formula 16, $X_2$ is a single bond, an oxygen atom, a sulfur atom, $-NR_1-$, $-S(=O)_2$, an alkylene group, an alkenylene group, an alkynylene group, $-C(=O)-X_1-$ or $-X_1-C(=O)-$, wherein $R_1$ is a hydrogen, an alkyl group, an alkenyl group, an alkynyl group, an alkoxy group or an aryl group, $X_1$ is a single bond, an oxygen atom, a sulfur atom, $-NR_2-$, $-S(=O)_2-$, an alkylene group, an alkenylene group or an alkynylene group, and W is an aryl group having 6 to 12 carbon atoms, which has a heterocyclic substituent.

The unit of Formula 16 may be represented by Formula 17.

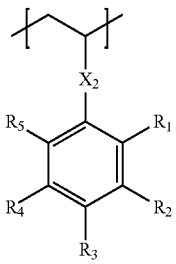

[Formula 17]

In Formula 17, $X_2$ is a single bond, an oxygen atom, a sulfur atom, —NR1-, —S(=O)2-, an alkylene group, an alkenylene group, an alkynylene group, —C(=O)—$X_1$— or —$X_1$—C(=O)—, wherein $R_1$ is a hydrogen, an alkyl group, an alkenyl group, an alkynyl group, an alkoxy group or an aryl group, and $X_1$ is a single bond, an oxygen atom, a sulfur atom, —NR2-, —S(=O)2-, an alkylene group, an alkenylene group or an alkynylene group. $R_1$ to $R_5$ may be each independently a hydrogen, an alkyl group, a haloalkyl group, a halogen atom and a heterocyclic substituent, and at least one of $R_1$ to $R_5$ is a heterocyclic substituent.

In Formula 17, at least one, for example, 1 to 3 or 1 to 2 of $R_1$ to $R_5$ are the heterocyclic substituents, and the other may be a hydrogen atom, an alkyl group or a halogen atom, a hydrogen atom or a halogen atom, or a hydrogen atom.

As the above-described heterocyclic substituent, a phthalimide-based substituent, a thiopene-based substituent, a thiazole-based substituent, a carbazol-based substituent, or an imidazol-based substituent may be used, but the present application is not limited thereto.

The block copolymer of the present application may include one or more of the above-described first blocks, and one or more of the above-described second blocks. Such a block copolymer may include two, three or more blocks. For example, the block copolymer may be a diblock copolymer including any one of the first blocks and the any one of the second blocks.

A specific method of preparing the above-described block copolymer is not particularly limited, and for example, the block copolymer may be prepared by performing a known method of preparing a block copolymer on a monomer capable of forming each block.

For example, the block copolymer may be prepared by a living radical polymerization (LRP) method using the monomer. For example, anionic polymerization for synthesizing a block copolymer using an organic rare earth metal complex as a polymerization initiator or using an organic alkali metal compound as a polymerization initiator in the presence of an inorganic acid salt such as a salt of an alkali metal or alkali earth metal, atom transfer radical polymerization (ATRP) using an atom transfer radical polymerizer as a polymerization control agent, activators regenerated by electron transfer (ARGET) atom transfer radical polymerization (ATRP) performing polymerization using an atom transfer radical polymerizer as a polymerization control agent in the presence of an organic or inorganic reducing agent generating electrons, initiators for continuous activator regeneration (ICAR) atom transfer radical polymerization (ATRP), reversible addition-fragmentation chain transfer (RAFT) using an inorganic reducing agent RAFT agent, or a method using an organic tellurium compound as an initiator may be used, and a suitable one may be selected from the above-described methods.

For example, the block copolymer may be prepared by a method including polymerizing a reactant including monomers capable of forming the block through living radical polymerization in the presence of a radical initiator and a living radical polymerization reagent.

A method of forming another block included in the copolymer as well as the block formed using the monomer during the preparation of a block copolymer is not particularly limited, and the block may be formed by selecting a suitable monomer by considering the type of a desired block.

The process of preparing a block copolymer may further include, for example, precipitating a polymerization product produced through the above-described process in a non-solvent.

The type of a radical initiator is not particularly limited, and therefore a radical initiator may be suitably selected by considering polymerization efficiency. For example, as a radical initiator, an azo compound such as azobisisobutyronitrile (AIBN) or 2,2'-azobis-(2,4-dimethylvaleronitrile), or a peroxide such as benzoyl peroxide (BPO) or di-t-butyl peroxide (DTBP) may be used.

The living radical polymerization may be performed in a solvent such as methylene chloride, 1,2-dichloroethane, chlorobenzene, dichlorobenzene, bezene, toluene, acetone, chloroform, tetrahydrofuran, dioxane, monoglyme, diglyme, dimethylformamide, dimethylsulfoxide or dimethylacetamide.

As a non-solvent, for example, an alcohol such as methanol, ethanol, normal propanol or isopropanol, a glycol such as ethyleneglycol, or an ether such as n-hexane, cyclohexane, n-heptane or petroleum ether may be used, but the present application is not limited thereto.

A method of forming a film on the above-described trench using the above-described block copolymer is not particularly limited, and to form a self-assembly structure, for example, a known method has been applied to form a polymer layer on a neutral-treated surface may be applied. For example, a polymer layer may be formed by preparing a coating solution by dispersing the block copolymer in a suitable solvent at a predetermined concentration, and coating the coating solution by a known coating method such as spin coating.

When necessary, an annealing process may be further performed to form a self-assembly structure on the polymer layer formed as described above. Such annealing may be performed by, for example, annealing or thermal-treating the layer. The annealing or thermal treatment may be performed based on a phase transition temperature or a glass transition temperature of the block copolymer, for example, at a temperature which is the same as or higher than the glass transition temperature or phase transition temperature. Time for such thermal treatment may be, but is not particularly limited to, for example, in a range of about 1 minute to 72 hours, and may be changed as necessary. Also, a temperature for the thermal treatment to the polymer thin film may be, for example, about 100 to 250° C., but may be changed by considering the block copolymer used herein.

In another embodiment, the formed layer may be annealed in a non-polar solvent and/or polar solvent at room temperature for about 1 minute to 72 hours.

Also, a method of manufacturing a patterned substrate of the present application may additionally include selectively removing any one block from the self-assembled block copolymer of the film formed in the trench as described above. For example, when the block copolymer includes the above-described first block and second block, the method may include selectively removing the first or second block from the block copolymer. Through such a process, for example, as shown in FIG. 3, only a block (B) which is not selectively removed may be present in a trench. The method of manufacturing a patterned substrate may further include etching the substrate, after any one or more blocks are selectively removed from the block copolymer.

In this method, a method of selectively removing any one block of the block copolymer is not particularly limited, and for example, a method of removing a relatively soft block by irradiating a polymer layer with a suitable electromagnetic wave such as an ultraviolet (UV) ray may be used. In this case, conditions for UV irradiation may be determined by the type of a block of the block copolymer, and for example, the UV irradiation may be performed by applying an UV ray with a wavelength of about 254 nm for 1 to 60 minutes.

Also, after the UV irradiation, removal of a segment degraded by the UV ray through treatment of the polymer layer with an acid may be performed.

Also, etching of the substrate using the polymer layer from which a block is selectively removed as a mask is not particularly limited, and may be performed through reactive ion etching using CF4/Ar ions. In this process, removal of the polymer layer from the substrate through oxygen plasma treatment may be further performed.

EFFECT

Figure 1:
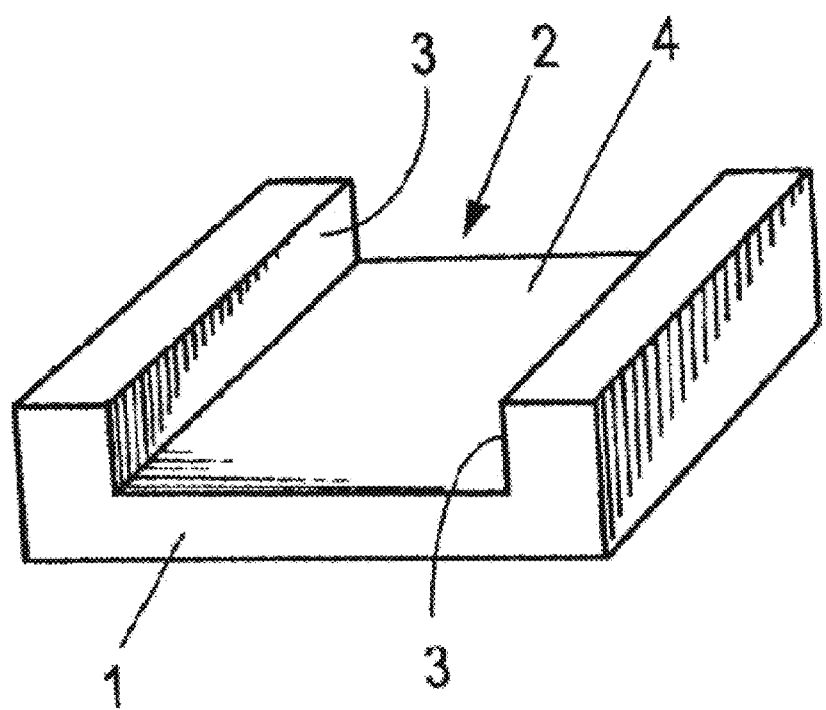
FIG. 1 shows an illustrative embodiment of a substrate on which a trench is formed.
Figure 2:
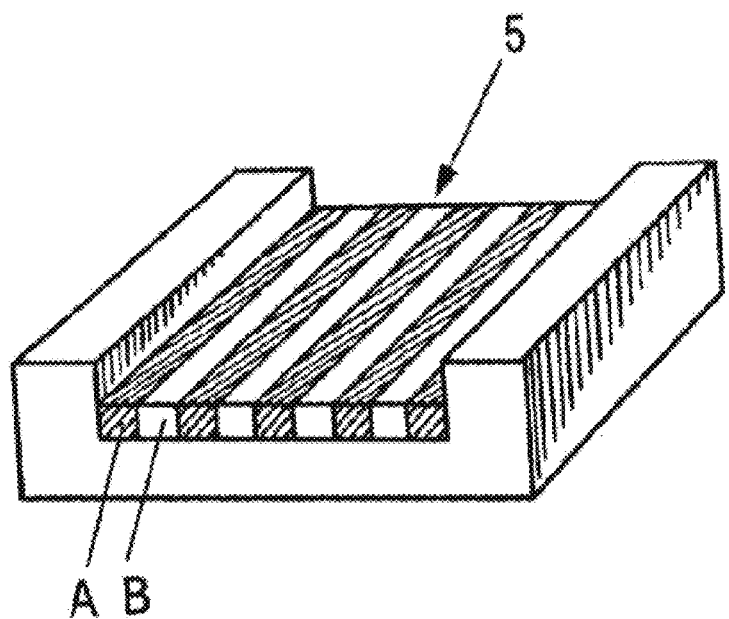
FIG. 2 schematically shows that a self-assembled polymer is formed in the trench of the substrate.
Figure 3:
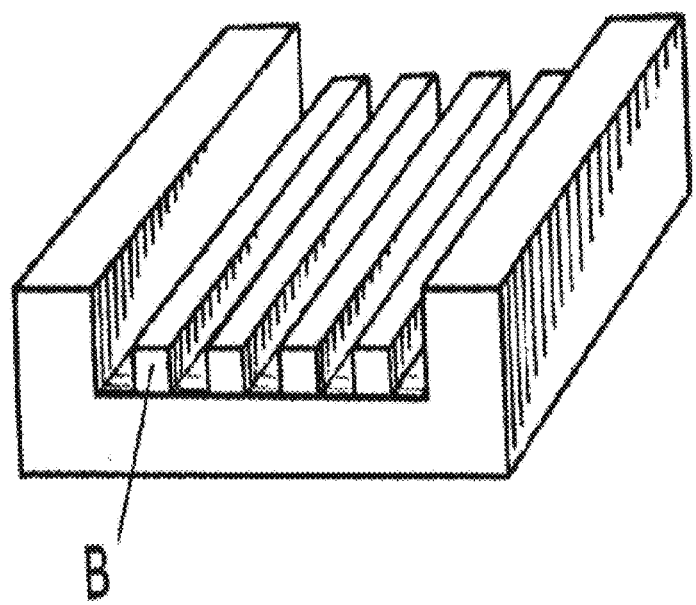
FIG. 3 schematically shows that any one block of the self-assembled block copolymer is selectively removed.
Figure 4:
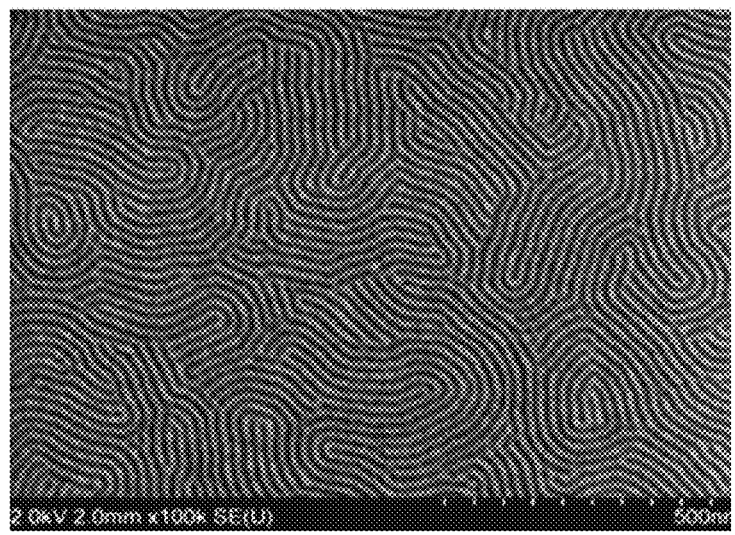
FIGS. 4 to 8 are SEM images of polymer layers formed by block copolymers of preparation examples 6 to 10.
Figure 5:
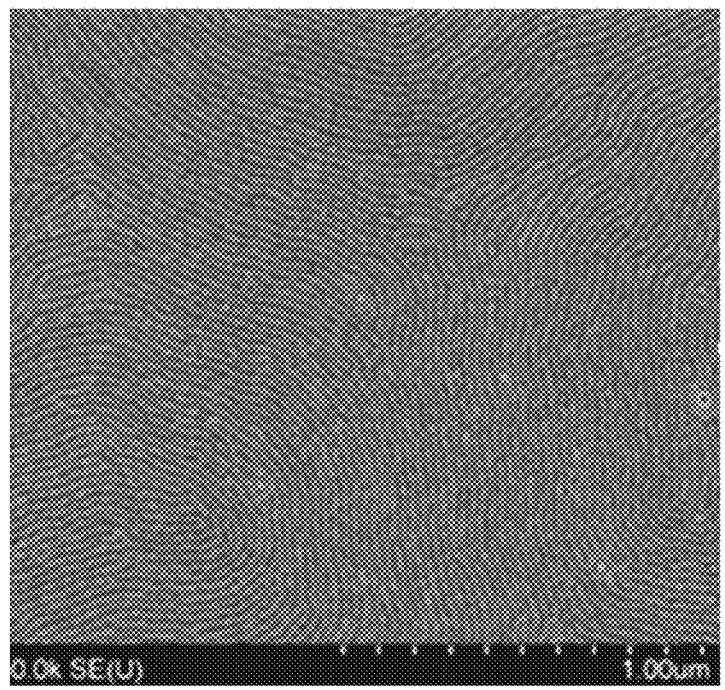
Figure 6:
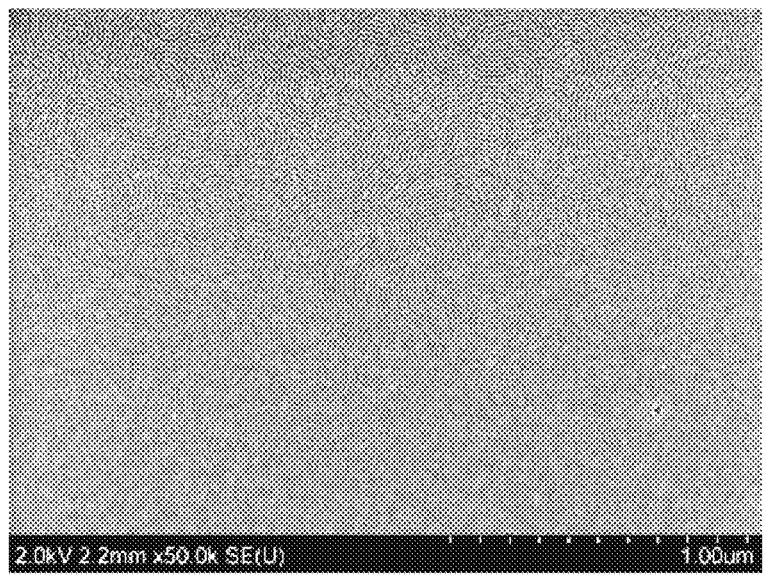
Figure 7:
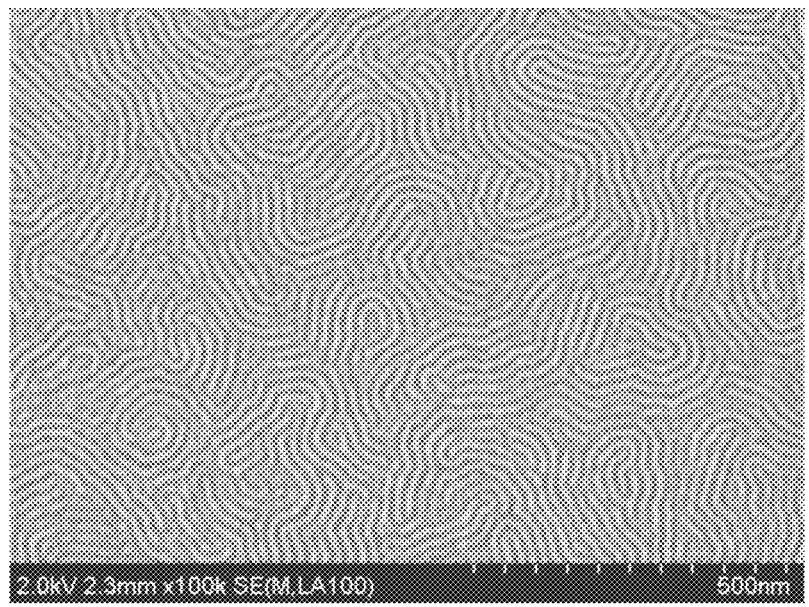
Figure 8:
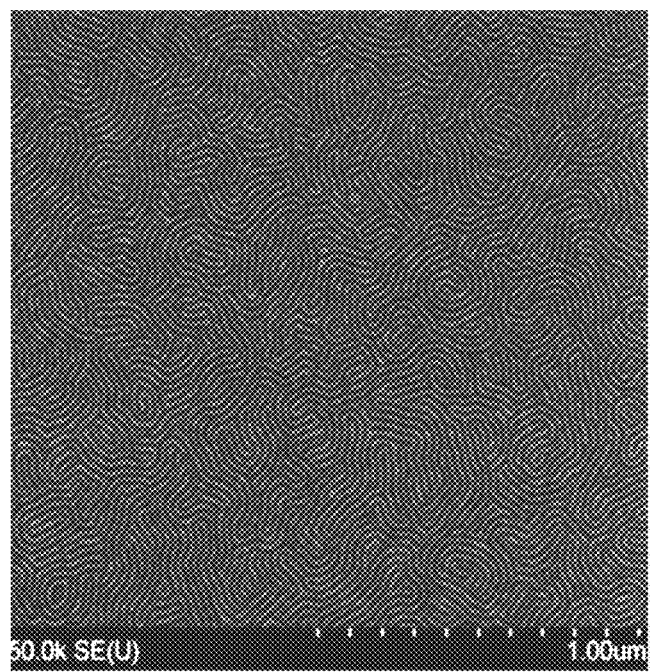

The present application relates to a method of manufacturing a patterned substrate. The method may be applied to a process of manufacturing devices such as an electronic device and an integrated circuit, or another use, for example, to manufacture an integrated optical system, a guidance and detection pattern of a magnetic domain memory, a flat panel display, a LCD, a thin film magnetic head or an organic light emitting diode, and used to construct a pattern on a surface to be used to manufacture a discrete tract medium such as an integrated circuit, a bit-patterned medium and/or a magnetic storage device such as a hard drive.

DETAILED DESCRIPTION OF EMBODIMENTS

Hereinafter, the present application will be described in further detail with reference to examples according to the present application, but the scope of the present application is not limited to the following examples.

1. NMR Analysis

NMR analysis was performed at room temperature using an NMR spectrometer including a Varian Unity Inova (500 MHz) spectrometer having a triple resonance 5 mm probe. A subject for analysis was diluted with a solvent ($CDCl_3$) for measuring NMR at a concentration of about 10 mg/ml, and chemical shift was expressed in ppm.

Abbreviations br=broad signal, s=singlet, d=doublet, dd=doublet of doublets, t=triplet, dt=doublet of triblets, q=quartet, p=quintet, m=multiplet.

2. Gel Permeation Chromatography (GPC)

A number average molecular weight (Mn) and a distribution of molecular weight were measured by GPC. A subject for analysis such as a block copolymer or macro initiator of Example or Comparative Example was put into 5 ml vial, and diluted with tetrahydrofuran (THF) to have a concentration of about 1 mg/mL. Afterward, a standard sample for Calibration and a sample for analysis were measured after passing through a syringe filter (pore size: 0.45 μm). As an analysis program, ChemStation produced by Agilent technologies was used, and an elution time for the sample was compared with a calibration curve, thereby obtaining a weight average molecular weight (Mw) and a number average molecular weight (Mn), and a ratio (Mw/Mn) was used to calculate a polydispersity index (PDI). Conditions for measuring GPC are as follows.
  <Conditions for Measuring GPC>
  Device: 1200 series produced by Agilent technologies
  Column: Two PLgel mixed B produced by Polymer laboratories
  Solvent: THF
  Column temperature: 35° C.
  Sample concentration: 1 mg/mL, 200 L injection
  Standard sample: Polystyrene (Mp: 3900000, 723000, 316500, 52200, 31400, 7200, 3940, 485)

3. Method for XRD Analysis

XRD analysis was performed by measuring a scattering intensity according to a scattering vector (q) by irradiating a sample with an X ray using a Pohang light source 4C beam line. As a sample, a powder-type block copolymer was obtained by purifying a synthesized block copolymer without specific pretreatment and drying the block copolymer in a vacuum oven for about one day, and put into a cell for XRD measurement. In XRD pattern analysis, an X ray having a vertical size of 0.023 mm and a horizontal size of 0.3 mm was used, and a 2D marCCD was used as a detector. A 2D diffraction pattern obtained by scattering was obtained an image. Information such as a scattering vector and a FWHM were obtained by analyzing the obtained diffraction pattern by numerical analysis method using the least square method. For the analysis, an origin program was applied, a part showing the least intensity in an XRD diffraction pattern was set as a baseline to make the intensity 0, a profile of the XRD pattern peak was fitted by Gaussian fitting, and the scattering vector and the FWHM was obtained from the fitted result. In the Gauss fitting, the R square was set to at least 0.96 or more.

4. Measurement of Surface Energy

Surface energy was measured using a drop-shape analyzer (DSA100, KRUSS). A coating solution was prepared by diluting a material for detection (polymer) with fluorobenzene at a solid content concentration of about 2 wt %, and the prepared coating solution was applied on a silicon wafer by spin coating to have a thickness of about 50 nm and a coating area of 4 cm² (width: 2 cm, length: 2 cm). The coating layer was dried at room temperature for about 1 hour, and then thermal-annealed at about 160° C. for about 1 hour. Deionized water having a known surface tension was dropped on the film undergoing the thermal annealing, and a mean value of five contact angles obtained by repeating measurement of contact angles five times. Likewise, diiodomethane having a known surface tension was dropped on the film undergoing the thermal annealing, and a mean value of five contact angles obtained by repeating measurement of contact angles five times. Surface energy was obtained by substituting a Strom value with respect to the surface tension of the solvent through the Owens-Wendt-Rabel-Kaelble method using the obtained mean values of the contact angles for the deionized water and diiodomethane. The value of surface energy for each block of the block copolymer was obtained by the above-described method applied to a homopolymer prepared only using a monomer for forming the block.

5. Measurement of Volume Fraction

The volume fraction of each block of the block copolymer was calculated based on a density, measured at room temperature, and a molecular weight, measured by GPC, of the block. Here, the density was measured by a buoyancy method, and specifically, calculated based on a weight of a sample for analysis after put into a solvent (ethanol) having a known weight and density in the air.

Preparation Example 1. Synthesis of Monomer (A)

A compound of Formula A (DPM-C12) was synthesized by the following method. Hydroquinone (10.0 g, 94.2 mmol) and 1-bromododecane (23.5 g, 94.2 mmol) were put into a 250 mL flask, dissolved in 100 mL acetonitrile, treated with an excessive amount of potassium carbonate to allow a reaction at 75° C. for about 48 hours under a nitrogen condition. After the reaction, remaining potassium carbonate was filtered to remove, and the acetonitrile used in the reaction was also removed. Here, a mixed solvent of dichloromethane (DCM) and water was added to work up, and a separated organic layer was dehydrated with MgSO$_4$. Therefore, a white solid product (4-dodecyloxyphenol; 9.8 g, 35.2 mmol) was obtained with an yield of about 37% through column chromatography using DCM.

<NMR Analysis Result>

$^1$H-NMR (CDCl$_3$): δ6.77 (dd, 4H); δ4.45 (s, 1H); δ3.89 (t, 2H); δ1.75 (p, 2H); δ1.43 (p, 2H); δ1.33-1.26 (m, 16H); δ0.88 (t, 3H).

Synthesized 4-dodecyloxyphenol (9.8 g, 35.2 mmol), methacrylic acid (6.0 g, 69.7 mmol), dicyclohexylcarbodiimide (DCC; 10.8 g, 52.3 mmol) and p-dimethylaminopyridine (DMAP; 1.7 g, 13.9 mmol) were put into a flask, and treated with 120 mL of methylenechloride to allow a reaction at room temperature for 24 hours under nitrogen. After the reaction was completed, a salt produced in the reaction (urea salt) was removed using a filter, and remaining methylenechloride was also removed. Debris was removed through column chromatography using hexane and dichloromethane (DCM) as moving phases, and then a product thereby was recrystallized in a mixed solvent of methanol and water (1:1 mixture), thereby obtaining a white solid product (7.7 g, 22.2 mmol) with an yield of 63%.

<NMR Analysis Result>

$^1$H-NMR (CDCl$_3$): δ7.02 (dd, 2H); δ6.89 (dd, 2H); δ6.32 (dt, 1H); δ5.73 (dt, 1H); δ3.94 (t, 2H); δ2.05 (dd, 3H); δ1.76 (p, 2H); δ1.43 (p, 2H); 1.34-1.27 (m, 16H); δ0.88 (t, 3H).

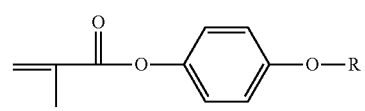

[Formula A]

In Formula A, R is a linear alkyl group having 12 carbon atoms.

Preparation Example 2. Synthesis of Monomer (B)

A compound of Formula B was synthesized by the method according to Preparation Example 1, except that 1-bromooctane, instead of 1-bromododecane, was used. The NMR analysis result for the compound is shown below.

<NMR Analysis Result>

$^1$H-NMR (CDCl$_3$): δ7.02 (dd, 2H); δ6.89 (dd, 2H); δ6.32 (dt, 1H); δ5.73 (dt, 1H); δ3.94 (t, 2H); δ2.05 (dd, 3H); δ1.76 (p, 2H); δ1.45 (p, 2H); 1.33-1.29 (m, 8H); δ0.89 (t, 3H).

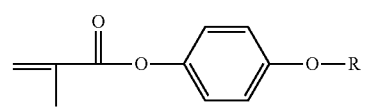

[Formula B]

In Formula B, R is a linear alkyl group having 8 carbon atoms.

Preparation Example 3. Synthesis of Monomer (C)

A compound of Formula C was synthesized by the method according to Preparation Example 1, except that 1-bromodecane, instead of 1-bromododecane, was used. The NMR analysis result for the compound is shown below.

<NMR Analysis Result>

$^1$H-NMR (CDCl$_3$): δ7.02 (dd, 2H); δ6.89 (dd, 2H); δ6.33 (dt, 1H); δ5.72 (dt, 1H); δ3.94 (t, 2H); δ2.06 (dd, 3H); δ1.77 (p, 2H); δ1.45 (p, 2H); 1.34-1.28 (m, 12H); δ0.89 (t, 3H).

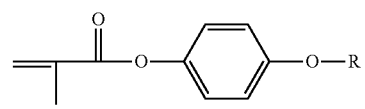

[Formula C]

In Formula C, R is a linear alkyl group having 10 carbon atoms.

Preparation Example 4. Synthesis of Monomer (D)

A compound of Formula D was synthesized by the method according to Preparation Example 1, except that 1-bromotetradecane, instead of 1-bromododecane, was used. The NMR analysis result for the compound is shown below.

<NMR Analysis Result>

$^1$H-NMR (CDCl$_3$): δ7.02 (dd, 2H); δ6.89 (dd, 2H); δ6.33 (dt, 1H); δ5.73 (dt, 1H); δ3.94 (t, 2H); δ2.05 (dd, 3H); δ1.77 (p, 2H); δ1.45 (p, 2H); 1.36-1.27 (m, 20H); δ0.88 (t, 3H)

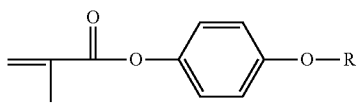

[Formula D]

In Formula D, R is a linear alkyl group having 14 carbon atoms.

Preparation Example 5. Synthesis of Monomer (E)

A compound of Formula E was synthesized by the method according to Preparation Example 1, except that 1-bromohexadetane, instead of 1-bromododecane, was used. The NMR analysis result for the compound is shown below.
<NMR Analysis Result>
$^1$H-NMR (CDCl$_3$): δ7.01 (dd, 2H); δ6.88 (dd, 2H); δ6.32 (dt, 1H); δ5.73 (dt, 1H); δ3.94 (t, 2H); δ2.05 (dd, 3H); δ1.77 (p, 2H); δ1.45 (p, 2H); 1.36-1.26 (m, 24H); δ0.89 (t, 3H)

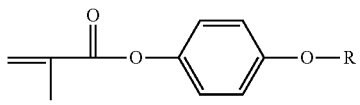

[Formula E]

In Formula E, R is a linear alkyl group having 16 carbon atoms.

Preparation Example 6. Synthesis of Block Copolymer 2.0 g of the monomer (A) of Preparation Example 1, 64 mg of a reversible addition-fragmentation chain transfer (RAFT) reagent, cyanoisopropyldithiobenzoate, 23 mg of a radical initiator, azobisisobutyronitrile (AIBN), and 5.34 ml of benzene were put into a 10 mL Schlenk flask, and stirred at room temperature for 30 minutes under a nitrogen atmosphere to allow an RAFT polymerization reaction at 70° C. for 4 hours. After the polymerization, a reaction solution was precipitated in 250 ml of methanol as an extraction solvent, and dried through decreased pressure filtration, thereby preparing a pink macroinitiator. The yield of the macroinitiator was about 82.6 wt %, and the number average molecular weight (Mn) and distribution of molecular weight (Mw/Mn) of the macroinitiator were 9,000 and 1.16, respectively. 0.3 g of the macroinitiator, 2.7174 g of a pentafluorostyrene monomer and 1.306 ml of benzene were put into a 10 mL Schlenk flask, and stirred at room temperature for 30 minutes under a nitrogen atmosphere to allow an RAFT polymerization reaction at 115° C. for 4 hours. After the polymerization, a reaction solution was precipitated in 250 ml of methanol as an extraction solvent, and dried through decreased pressure filtration, thereby preparing a light pink block copolymer. The yield of the block copolymer was about 18 wt %, and the number average molecular weight (Mn) and distribution of molecular weight (Mw/Mn) of the block copolymer were 16,300 and 1.13, respectively. The block copolymer includes a first block derived from the monomer (A) of Preparation Example 1 and a second block derived from the pentafluorostyrene monomer.

Preparation Example 7. Synthesis of Block Copolymer

A block copolymer was prepared using a macroinitiator and a pentafluorostyrene as monomers by the method according to Preparation Example 6, except that the monomer (B) of Preparation Example 2, instead of the monomer (A) of Preparation Example 1, was used. The block copolymer includes a first block derived from the monomer (B) of Preparation Example 2 and a second block derived from the pentafluorostyrene monomer.

Preparation Example 8. Synthesis of Block Copolymer

A block copolymer was prepared using a macroinitiator and a pentafluorostyrene as monomers by the method according to Preparation Example 6, except that the monomer (C) of Preparation Example 3, instead of the monomer (A) of Preparation Example 1, was used. The block copolymer includes a first block derived from the monomer (C) of Preparation Example 3 and a second block derived from the pentafluorostyrene monomer.

Preparation Example 9. Synthesis of Block Copolymer

A block copolymer was prepared using a macroinitiator and a pentafluorostyrene as monomers by the method according to Preparation Example 6, except that the monomer (D) of Preparation Example 4, instead of the monomer (A) of Preparation Example 1, was used. The block copolymer includes a first block derived from the monomer (D) of Preparation Example 4 and a second block derived from the pentafluorostyrene monomer.

Preparation Example 10. Synthesis of Block Copolymer

A block copolymer was prepared using a macroinitiator and a pentafluorostyrene as monomers by the method according to Preparation Example 6, except that the monomer (E) of Preparation Example 5, instead of the monomer (A) of Preparation Example 1, was used. The block copolymer includes a first block derived from the monomer (E) of Preparation Example 5 and a second block derived from the pentafluorostyrene monomer.

GPC results for the macroinitiators and the block copolymers prepared in the above Preparation Examples are summarized and listed in Table 1.

TABLE 1

| | | Preparation Example | | | | |
|---|---|---|---|---|---|---|
| | | 6 | 7 | 8 | 9 | 10 |
| MI | Mn | 9000 | 9300 | 8500 | 8700 | 9400 |
| | PDI | 1.16 | 1.15 | 1.17 | 1.16 | 1.13 |
| BCP | Mn | 16300 | 19900 | 17100 | 17400 | 18900 |
| | PDI | 1.13 | 1.20 | 1.19 | 1.17 | 1.17 |

MI: macroinitiator
BCP: block copolymer
Mn: number average molecular weight
PDI: polydispersity index Experiment Example 1. X-Ray Diffraction Analysis Results for analyzing XRD patterns for the block copolymers by the above-described methods are summarized and listed in Table 2.

TABLE 2

| | Preparation Example | | | | |
|---|---|---|---|---|---|
| | 6 | 7 | 8 | 9 | 10 |
| q peak value (unit: nm$^{-1}$) | 1.96 | 2.41 | 2.15 | 1.83 | 1.72 |
| FWHM (unit: nm$^{-1}$) | 0.57 | 0.72 | 0.63 | 0.45 | 0.53 |

Experiment Example 2. Evaluation of Self Assembling Properties

A coating solution prepared by diluting the block copolymer prepared in the preparation example 6, 7, 8, 9 or 10 in toluene so as to have 1 weight % of solid content was spin coated on a silicon wafer (coating area: width×length=1.5 cm×1.5 cm) so as to have a thickness of about 50 nm, the coated coating solution was dried under a room temperature for about an hour and then was subjected to a thermal annealing at 160° C. for about an hour so as to form a self assembled layer. The SEM (Scanning Electron Microscope) analysis was performed to each of the formed layers. FIGS. 4 to 8 are the SEM images of the layers formed by the block copolymers of preparation examples 6 to 10. As confirmed from the figures, in a case of the block copolymer, a polymer layer that was self assembled in a line shape was effectively formed.

Experiment Example 3. Evaluation of Physical Properties of Block Copolymer

Results of evaluating properties of the block copolymers prepared in Preparation Examples 6 to 10 by the method described above are summarized and listed in Table 3.

TABLE 3

| | | Preparation Example | | | | |
|---|---|---|---|---|---|---|
| | | 6 | 7 | 8 | 9 | 10 |
| First block | SE | 30.83 | 31.46 | 27.38 | 26.924 | 27.79 |
| | De | 1 | 1.04 | 1.02 | 0.99 | 1.00 |
| | VF | 0.66 | 0.57 | 0.60 | 0.61 | 0.61 |
| Second block | SE | 24.4 | 24.4 | 24.4 | 24.4 | 24.4 |
| | De | 1.57 | 1.57 | 1.57 | 1.57 | 1.57 |
| | VF | 0.34 | 0.43 | 0.40 | 0.39 | 0.39 |
| SE difference | | 6.43 | 7.06 | 2.98 | 2.524 | 3.39 |
| De difference | | 0.57 | 0.53 | 0.55 | 0.58 | 0.57 |
| Chain-forming atom | | 12 | 8 | 10 | 14 | 16 |
| n/D | | 3.75 | 3.08 | 3.45 | 4.24 | 4.44 |

SE: surface energy(unit: mN/m)
De: density(unit: g/cm$^3$)
VF: volume fraction
SE difference: absolute value of difference in surface energy between first block and second block
De difference: absolute value of difference in density between first block and second block
Chain-forming atom: the number of chain-forming atoms of first block
n/D: value calculated by Equation 1 (nq/(2 × π)) (n: the number of chain-forming atoms, q: value of scattering vector showing peak having the largest peak area in range of scattering vector from 0.5 nm$^{-1}$ to 10 nm$^{-1}$)
Ref: polystyrene-polymethylmethacrylate block copolymer (first block: polystyrene block, second block: polymethylmethacrylate block)

Example 1

Figure 9:
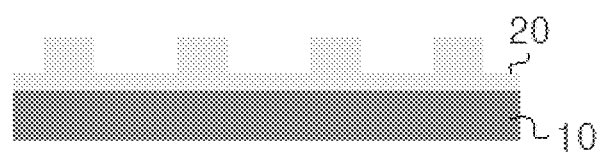
FIG. 9 shows a structure including a substrate and a mesa structure formed on the surface of the substrate.

Patterning of a substrate by using the block copolymer of the preparation example 6 was performed as below. As the substrate, a silicon wafer was used. A layer of SiO$_2$ was formed on the substrate so as to have a thickness of about 200 nm by a conventional depositing method. Then, the BARC (Bottom Anti Reflective Coating) having a thickness of about 60 nm was coated on the layer of SiO$_2$ and then the PR (photoresist) layer (used for KrF, positive-tone resist layer) having a thickness of about 400 nm was coated thereon. Then the PR layer was patterned by a KrF stepper light exposure method. Then, the BARC layer and the layer of SiO$_2$ were patterned by a RIE (Reactive Ion Etching) method using the patterned PR layer as a mask and residues of the BARC layer and the layer of SiO$_2$ were eliminated so as to form the mesa structure. FIG. 9 shows a structure including the substrate (10) and the mesa structure (20) formed on the surface of the substrate, formed by the above process. The interval (D) between the mesa structures was about 150 nm, the height (H) of the mesa structure was about 100 nm and the width (W) of the mesa structure was about 150 nm.

A polymer layer using the block copolymer of the preparation example 6 was formed within the trench formed by the mesa structures. Any additional treatment such as forming the neutral brush layer was not performed on the trench.

Figure 10:
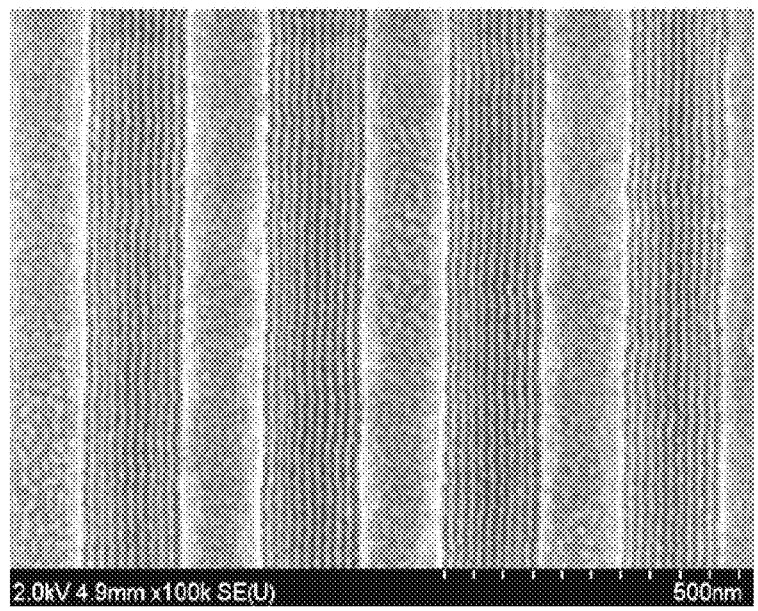
FIG. 10 is an SEM image of a self assembled structure formed in Example 1.

Specifically, a coating solution prepared by diluting the block copolymer in toluene so as to have 1.5 weight % of solid content was spin coated, the coated coating solution was dried under a room temperature for about an hour and then was subjected to a thermal annealing at about 160° C. to 250° C. for about an hour so as to form a self assembled layer. FIG. 10 is a SEM (Scanning Electron Microscope) image of the self assembled structure formed as above, and from the figure, it can be confirmed that a linear property of the self assembled lamella structure has been improved.

Example 2

A self-assembled polymer layer was formed by the same method as in Example 1, except that the block copolymer of Preparation Example 7, instead of the block copolymer of Preparation Example 6, was used. As a result of confirming the SEM image, it was confirmed that a suitable self-assembly structure is formed as described in Example 1.

Example 3

A self-assembled polymer layer was formed by the same method as in Example 1, except that the block copolymer of Preparation Example 8, instead of the block copolymer of Preparation Example 6, was used. As a result of confirming the SEM image, it was confirmed that a suitable self-assembly structure is formed as described in Example 1.

Example 4

A self-assembled polymer layer was formed by the same method as in Example 1, except that the block copolymer of Preparation Example 9, instead of the block copolymer of Preparation Example 6, was used. As a result of confirming the SEM image, it was confirmed that a suitable self-assembly structure is formed as described in Example 1.

Example 5

A self-assembled polymer layer was formed by the same method as in Example 1, except that the block copolymer of Preparation Example 10, instead of the block copolymer of Preparation Example 6, was used. As a result of confirming the SEM image, it was confirmed that a suitable self-assembly structure is formed as described in Example 1.

What is claimed is:

1. A method of manufacturing a patterned substrate, comprising:
   forming a self-assembled structure of a block copolymer within a trench on a surface of a substrate,
   wherein the block copolymer includes a first block having a ring structure and a side chain substituted on the ring structure, the side chain having 3 or more chain-forming atoms,
   wherein an interface between adjacent domains of the block copolymer in the self-assembled structure is substantially vertical with respect to the surface of the substrate,
   wherein the trench is formed between mesa structures, wherein the mesa structures are arranged so as to have an interval distance (D) between adjacent mesa structures on the substrate; and wherein the surface of the trench which is directly contacted by the self-assembled structure is not neutralized by a neutral brush layer to facilitate the substantially vertical orientation of the interface in the self-assembled structure,
   wherein the first block having the unit represented by Formula 1:

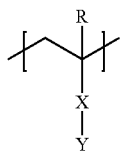

[Formula 1]

where R is a hydrogen or an alkyl group, X is an oxygen atom, a sulfur atom, —S(=O)$_2$—, a carbonyl group, an alkylene group, an alkenylene group, an alkynylene group, —C(=O)—X$_1$— or —X$_1$—C(=O)—, in which X$_1$ is an oxygen atom, a sulfur atom, —S(=O)$_2$—, an alkylene group, an alkenylene group or an alkynylene group, and Y is a monovalent substituent comprising the ring structure with which the side chain is substituted.

2. The method of claim 1, wherein the trench is formed by a method, comprising:
   forming a mesa structure-forming material layer, an anti-reflection layer, and a resist layer sequentially on the substrate;
   patterning the resist layer; and
   etching the mesa structure-forming material layer using the patterned resist layer as a mask to form the trench.

3. The method of claim 2, wherein the etching of the mesa structure-forming material layer comprises:
   reactive ion etching the mesa structure-forming material layer.

4. The method of claim 1, wherein a ratio (D/H) of the interval distance (D) to a height (H) ranges from 0.1 to 10.

5. The method of claim 1, wherein a ratio (D/W) of the interval distance (D) to a width (W) of the mesa structure ranges from 0.5 to 10.

6. The method of claim 1, wherein the self-assembled structure of the block copolymer is a lamella structure and the interval distance (D) ranges from 1 L to 20 L, and wherein the L is a pitch of the lamella structure.

7. The method of claim 1, wherein the self-assembled structure of the block copolymer is a lamella structure and has a thickness ranging from 1 L to 10 L, wherein the L is a pitch of the lamella structure.

8. The method of claim 1, wherein the self-assembled structure of the block copolymer is a lamella structure.

9. The method of claim 1, wherein the block copolymer further comprises a second block different from the first block, and wherein the first block shows a peak at an azimuthal angles of −90 to −70 degrees and of 70 to 90 degrees in a diffraction pattern of a scattering vector of 12 to 16 nm$^{-1}$ in a GIWAXS spectrum.

10. The method of claim 1, wherein the block copolymer further comprises a second block having a different chemical structure from the first block, and wherein the first block shows a melting transition peak or isotropic transition peak in a range of −80 to 200° C. through differential scanning calorimetry (DSC) analysis.

11. The method of claim 1, wherein the block copolymer further comprises a second block having a different chemical structure from the first block, and wherein the first block shows a peak having a full width at half maximum (FWHM) of 0.2 to 0.9 nm$^{-1}$ in a scattering vector (q) range of 0.5 to 10 nm$^{-1}$ through XRD analysis.

12. The method of claim 1, wherein the block copolymer further comprises a second block having a different chemical structure from the first block, wherein the first block includes a side chain, and wherein the number of chain-forming atoms (n) of the side chain and the scattering vector (q) obtained by XRD analysis performed on the first block, satisfy Equation 2:

$$3 \text{ to } 5 \text{ nm}^{-1} = nq/(2 \times \pi)$$ [Equation 2]

where n is the number of chain-forming atoms of the side chain, q is the smallest scattering vector (q) in which a peak is shown through XRD analysis performed on a block including the side chain, or a scattering vector (q) showing a peak having the largest peak area.

13. The method of claim 1, wherein the block copolymer further comprises a second block having a different chemical structure from the first block, and wherein the absolute value of a difference in surface energy between the first block and the second block is 10 mN/m or less.

14. The method of claim 1, wherein the block copolymer further comprises a second block having a different chemical structure from the first block, and wherein the absolute value of a difference in density between the first block and the second block is 0.25 g/cm$^3$ or more.

15. The method of claim 1, wherein the block copolymer further comprises a second block different from the first block, and wherein a volume fraction of the first block is in a range of 0.2 to 0.6, and a volume fraction of the second block is in a range of 0.4 to 0.8.

16. The method of claim 1, wherein the side chain has 5 or more chain-forming atoms.

17. The method of claim 1, wherein the ring structure does not include a halogen atom.

18. The method of claim 16, wherein the block copolymer further comprises a second block different from the first block, wherein the second block includes 3 or more halogen atoms.

19. The method of claim 18, wherein the second block comprises a ring structure, and the halogen atoms are substituted in the ring structure.

20. The method of claim 1, wherein Y of Formula 1 is represented by Formula 2:

[Formula 2]

where P is an arylene group or a cycloalkylene group, Q is a single bond, an oxygen atom or —NR$_3$—, in which R$_3$ is a hydrogen, an alkyl group, an alkenyl group, an alkynyl group, an alkoxy group or an aryl group, Z is the chain having three or more chain-forming atoms when P is an arylene group, or the chain having 8 or more chain-forming atoms when P is a cycloalkylene group.

21. The method of claim 20, wherein P of Formula 2 is an arylene group having 6 to 12 carbon atoms.

22. The method of claim 1, wherein the block copolymer further comprises a second block having the unit represented by Formula 5:

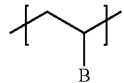

[Formula 5]

where B is a monovalent substituent having an aromatic structure including one or more halogen atoms.

23. The method of claim 1, further comprising:
selectively removing any one block of the block copolymer, which forms the self-assembly structure.

24. The method of claim 23, further comprising: etching the substrate, after one block of the block copolymer is selectively removed.

* * * * *